(12) United States Patent
Malicet et al.

(10) Patent No.: US 11,712,486 B2
(45) Date of Patent: Aug. 1, 2023

(54) COMPOSITIONS AND METHODS FOR CANCER IMAGING AND RADIOTHERAPY

(71) Applicants: VECT-HORUS, Marseilles (FR); CENTRE NATIONAL DE LA RECHERCHE SCIENTIFIQUE, Paris (FR); UNIVERSITE D'AIX-MARSEILLE, Marseilles (FR)

(72) Inventors: Cédric Malicet, Marseilles (FR); Pascaline Lecorche, Marseilles (FR); Jonathan Nowak, Marseilles (FR); Marion David, Marseilles (FR); Jamal Temsamani, Nimes (FR); Michel Khrestchatisky, Marseilles (FR)

(73) Assignees: VECT-HORUS, Marseilles (FR); CENTRE NATIONAL DE LA RECHERCHE SCIENTIFIQUE, Paris (FR); UNIVERSITE D'AIX-MARSEILLE, Marseilles (FR)

( * ) Notice: Subject to any disclaimer, the term of this patent is extended or adjusted under 35 U.S.C. 154(b) by 0 days.

(21) Appl. No.: 16/479,234

(22) PCT Filed: Jan. 30, 2018

(86) PCT No.: PCT/EP2018/052234
§ 371 (c)(1),
(2) Date: Jul. 19, 2019

(87) PCT Pub. No.: WO2018/138372
PCT Pub. Date: Aug. 2, 2018

(65) Prior Publication Data
US 2019/0351079 A1 Nov. 21, 2019

(30) Foreign Application Priority Data
Jan. 30, 2017 (EP) ..................... 17305098

(51) Int. Cl.
| | | |
|---|---|---|
| *A61K 51/08* | (2006.01) | |
| *A61K 51/04* | (2006.01) | |
| *C07K 7/06* | (2006.01) | |
| *G01N 33/574* | (2006.01) | |
| *G01N 33/60* | (2006.01) | |
| *G01N 33/92* | (2006.01) | |

(52) U.S. Cl.
CPC .......... *A61K 51/088* (2013.01); *A61K 51/048* (2013.01); *C07K 7/06* (2013.01); *G01N 33/57438* (2013.01); *G01N 33/60* (2013.01); *G01N 33/92* (2013.01); *A61K 2121/00* (2013.01); *A61K 2123/00* (2013.01)

(58) Field of Classification Search
CPC ...... A61K 51/00; A61K 51/08; A61K 51/088; A61K 2121/00; A61K 2123/00; A61K 49/00; A61K 49/0056; A61K 51/048; A61P 35/00; C07K 7/06; C07K 7/08; C07K 19/00; C07K 14/705; G01N 33/60; G01N 33/92; G01N 33/57438
USPC .......... 424/1.11, 1.49, 1.65, 1.69, 1.81, 1.85, 424/1.89, 9.1, 9.2, 90.3, 9.4, 9.5, 9.6, 9.3; 534/7, 10–16; 530/300; 514/1, 1.1, 19.2, 514/19.3, 19.4, 19.5, 19.6, 21.3, 21.4, 514/21.5, 21.6, 21.7, 21.8, 21.9, 21.91
See application file for complete search history.

(56) References Cited

U.S. PATENT DOCUMENTS

| | | | | |
|---|---|---|---|---|
| 5,736,120 A | * | 4/1998 | Srinivasan | A61K 51/088 424/1.65 |
| 7,481,993 B2 | * | 1/2009 | Cyr | A61K 51/088 424/1.69 |
| 8,729,029 B2 | * | 5/2014 | Khrestchatisky | C07K 7/64 514/21.3 |
| 8,877,716 B2 | * | 11/2014 | Vlieghe | A61P 25/28 514/21.3 |
| 2012/0251444 A1 | * | 10/2012 | Starr | A61P 37/06 514/3.3 |
| 2013/0108548 A1 | | 5/2013 | Vlieghe et al. | |
| 2014/0243499 A1 | | 8/2014 | Khrestchatisky et al. | |

FOREIGN PATENT DOCUMENTS

| | | |
|---|---|---|
| WO | WO 2014/060601 | 4/2014 |
| WO | WO 2015/031673 | 3/2015 |

OTHER PUBLICATIONS

Malcor et al, J. of Medicinal Chemistry, vol. 55, pp. 2227-2241 (Year: 2012).*
Jaquot et al, Mol. Pharm., vol. 13, No. 12, pp. 4094-4105 (published online Sep. 22, 2016) (Year: 2016).*
Tanaka, K. et al. "PET (positron emission tomography) imaging of biomolecules using metal-DOTA complexes: a new collaborative challenge by chemists, biologists, and physicians for future diagnostics and exploration of in vivo dynamics" *Organic & Biomolecular Chemistry*, 2008, pp. 815-828, vol. 6, No. 5.
Written Opinion in International Application No. PCT/EP2018/052234, dated Apr. 24, 2018, pp. 1-7.

* cited by examiner

*Primary Examiner* — D. L. Jones
(74) *Attorney, Agent, or Firm* — Saliwanchik, Lloyd & Eisenschenk

(57) ABSTRACT

The present invention relates to a conjugated compound comprising a marker M pharmaceutically acceptable, and a peptide or pseudo-peptide P having at most 30 amino acid residues and able to bind the Low-Density Lipoprotein Receptor (LDLR) and to its use in a method of labelling and/or detecting and/or treating cancerous cells in a subject by administration of the conjugated compound to the subject an analysis of the presence and/or the amount of marker.

9 Claims, 21 Drawing Sheets

Specification includes a Sequence Listing.

A.
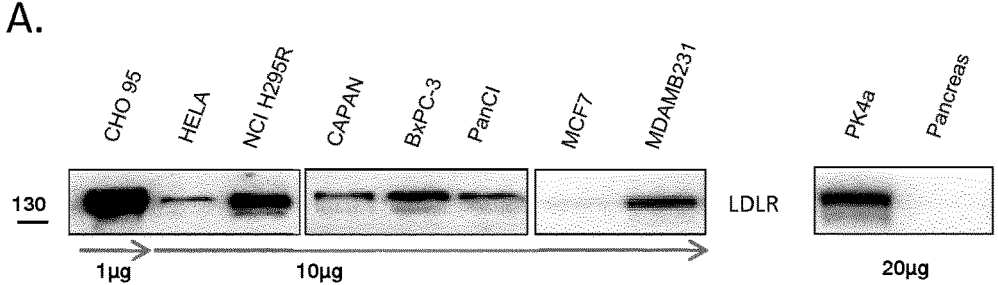
B.
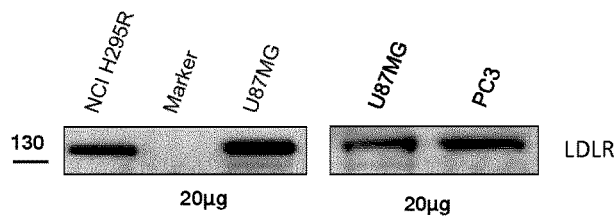
Figure 1
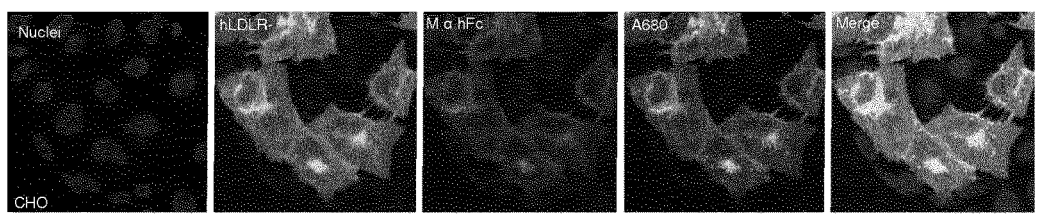
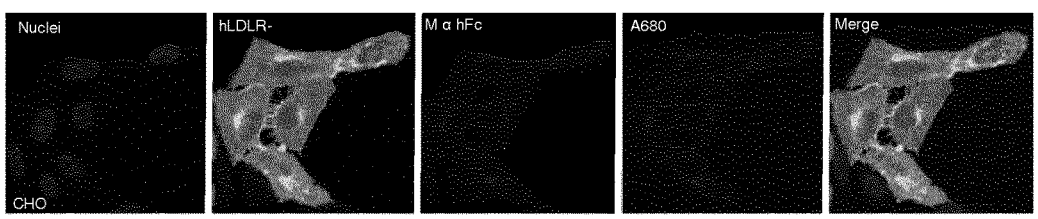
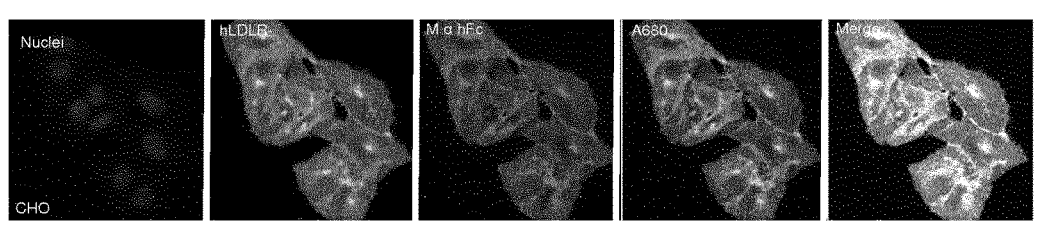
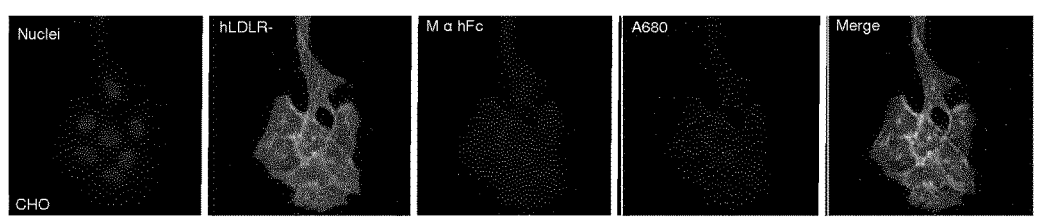
Figure 2

B
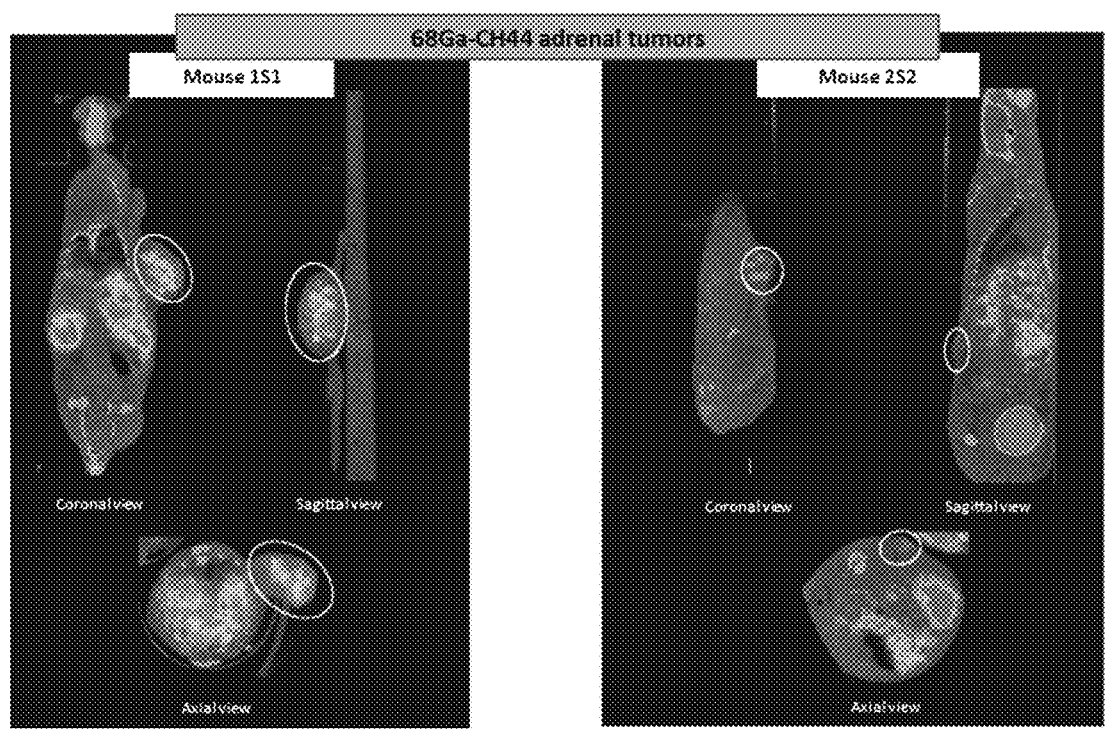
C
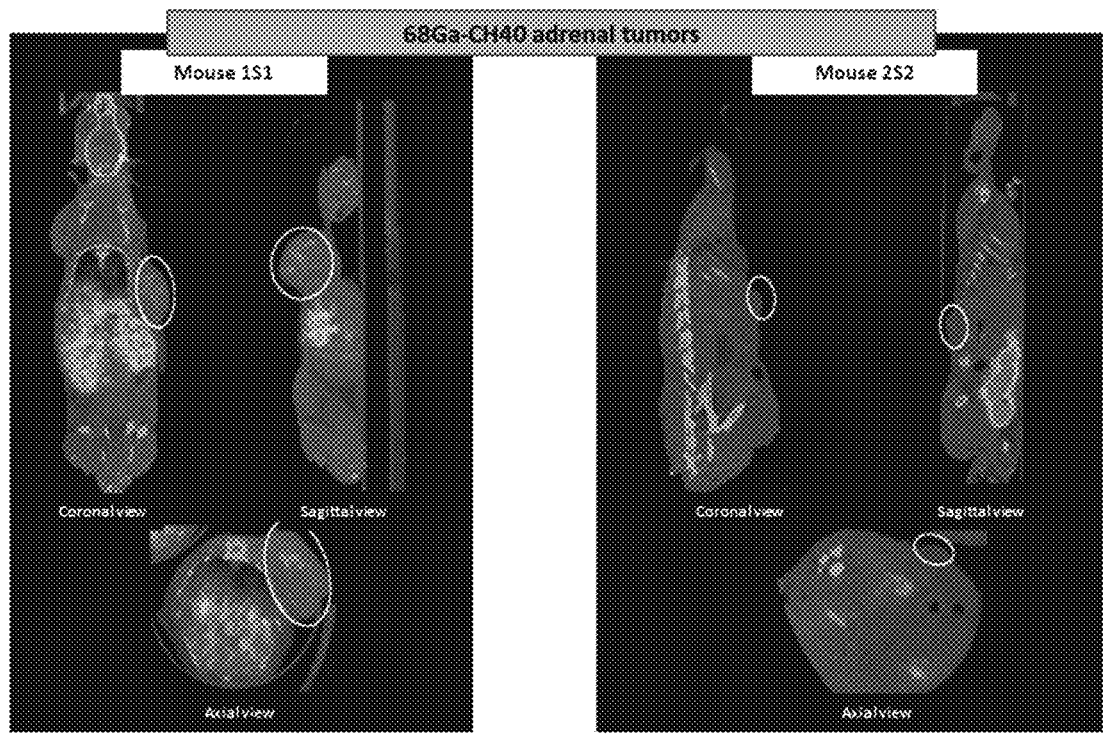
Figure 6 (B and C)

A
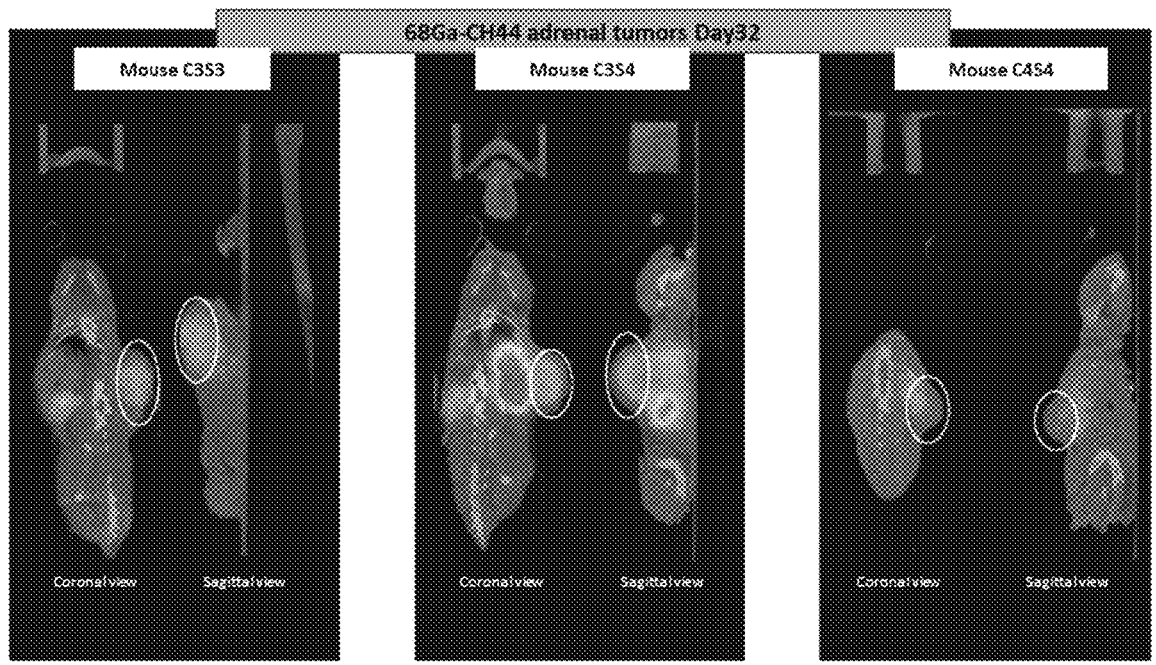
B
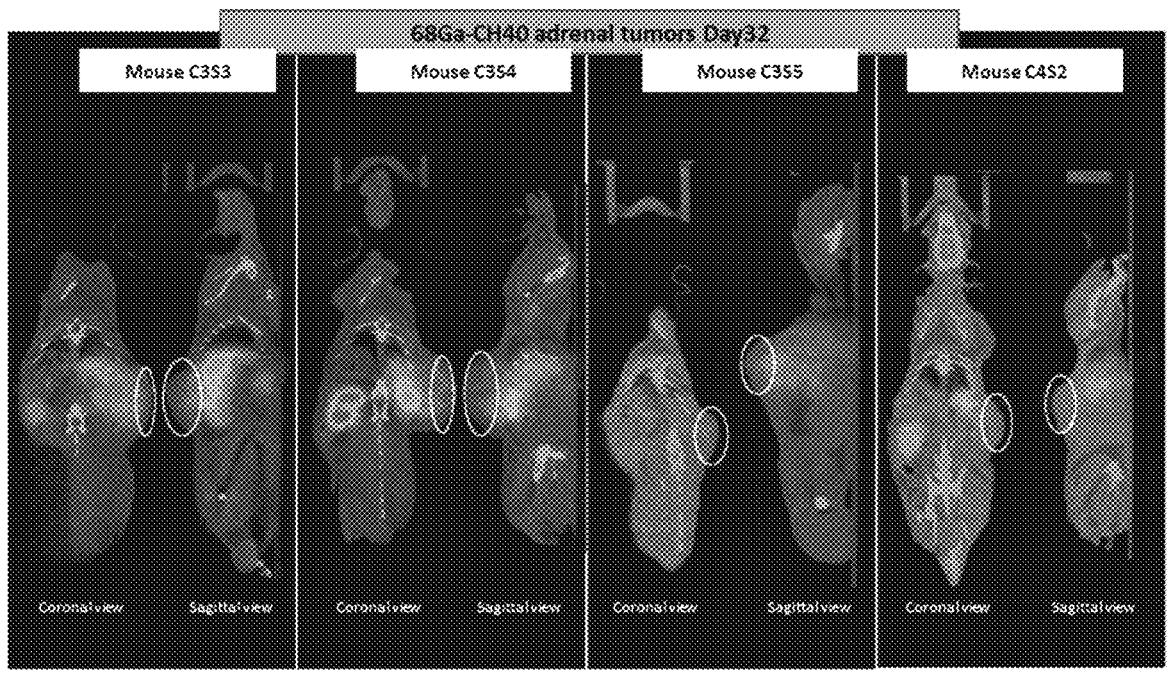
Figure 7 (A and B)

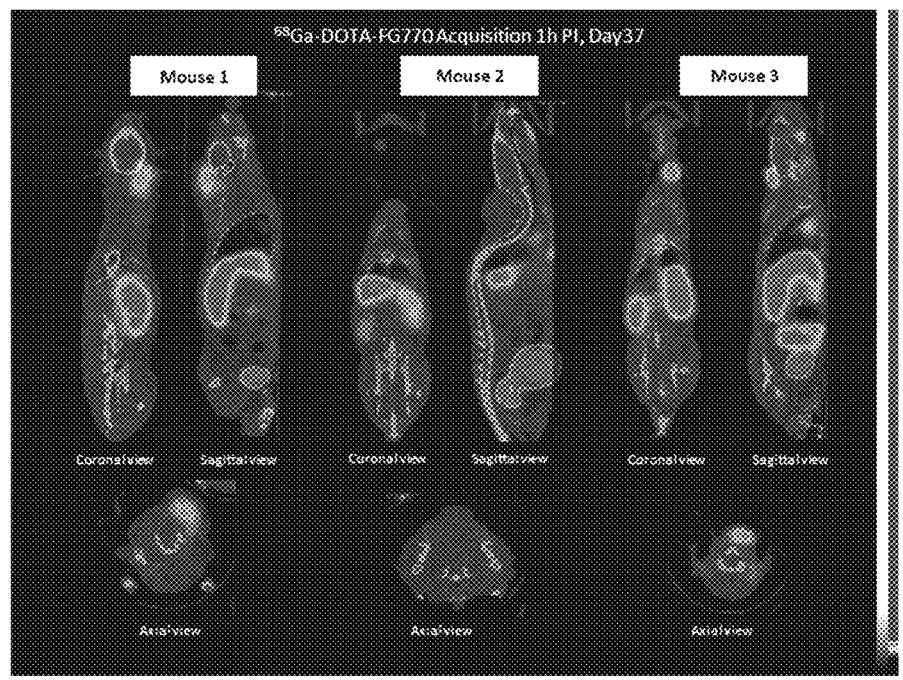
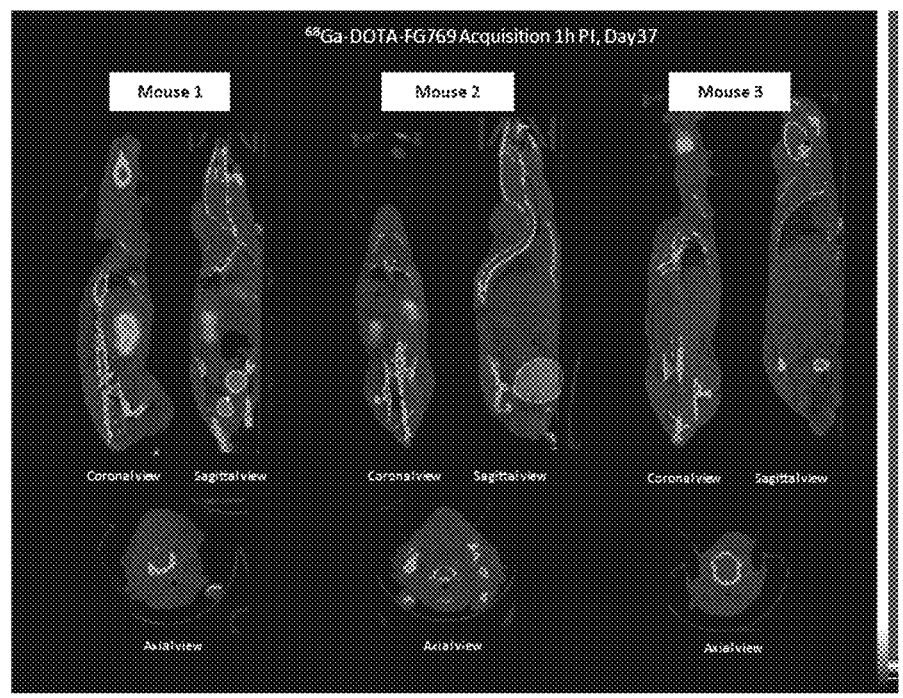
Figure 8 (A and B)

A.
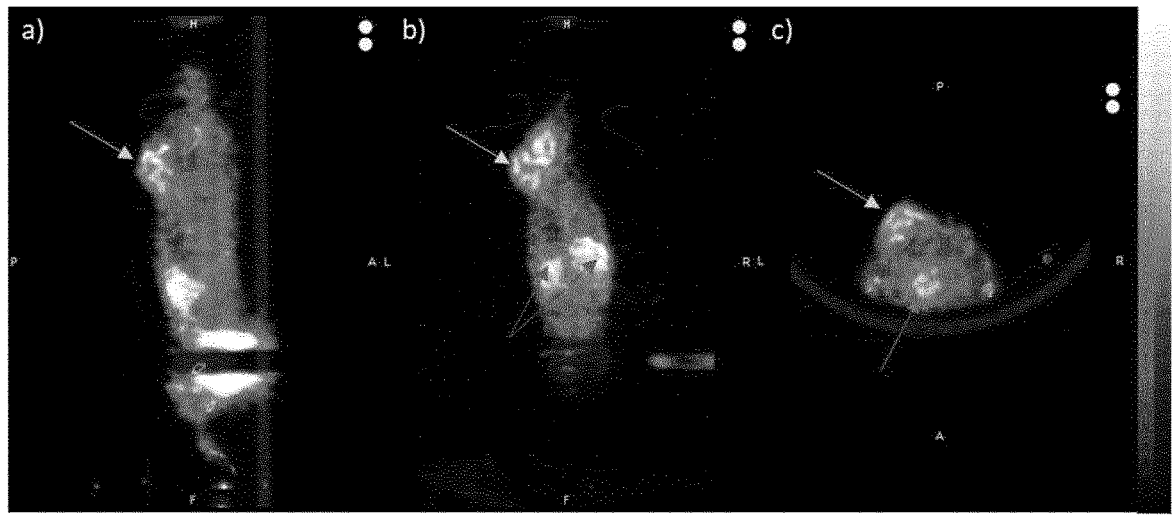
B.
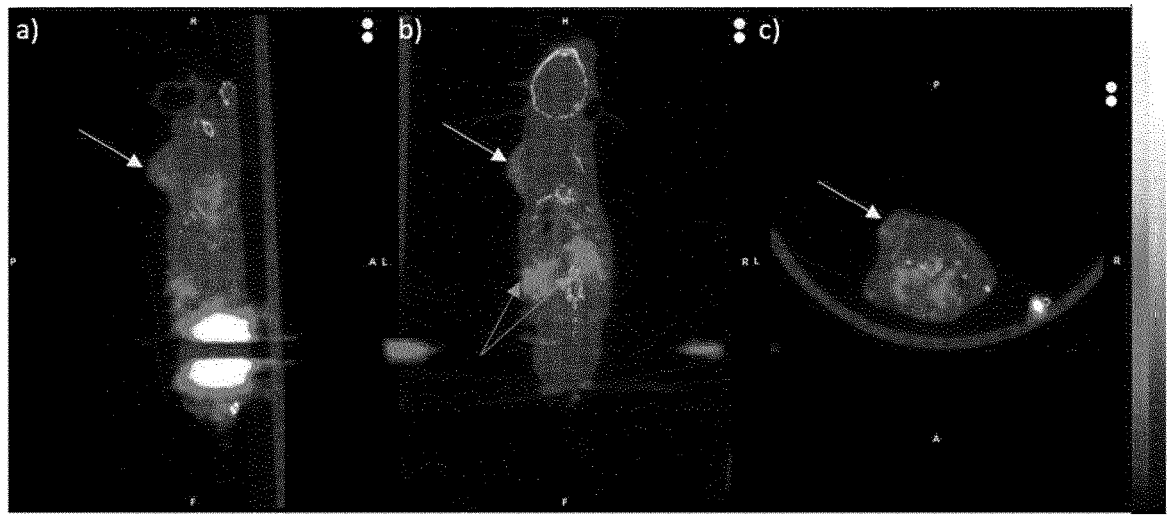
Figure 13

SEQUENCE LISTING

<160> NUMBER OF SEQ ID NOS: 16

<210> SEQ ID NO 1
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X is (D)-Cys
<220> FEATURE:
<221> NAME/KEY: MISC_FEATURE
<222> LOCATION: (3)..(3)
<223> OTHER INFORMATION: X is Thz
<220> FEATURE:
<221> NAME/KEY: MISC_FEATURE
<222> LOCATION: (8)..(8)
<223> OTHER INFORMATION: X is Pen

<400> SEQUENCE: 1

Xaa Met Xaa Arg Leu Arg Gly Xaa
1               5

<210> SEQ ID NO 2
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X is (D)-Cys
<220> FEATURE:
<221> NAME/KEY: MISC_FEATURE
<222> LOCATION: (3)..(3)
<223> OTHER INFORMATION: X is Thz
<220> FEATURE:
<221> NAME/KEY: MISC_FEATURE
<222> LOCATION: (7)..(7)
<223> OTHER INFORMATION: X is Sar
<220> FEATURE:
<221> NAME/KEY: MISC_FEATURE
<222> LOCATION: (8)..(8)
<223> OTHER INFORMATION: X is Pen

<400> SEQUENCE: 2

Xaa Met Xaa Arg Leu Arg Xaa Xaa
1               5

<210> SEQ ID NO 3
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X is (D)-Cys
<220> FEATURE:
<221> NAME/KEY: MISC_FEATURE
<222> LOCATION: (3)..(3)
<223> OTHER INFORMATION: X is Pip
<220> FEATURE:
<221> NAME/KEY: MISC_FEATURE
<222> LOCATION: (7)..(7)
<223> OTHER INFORMATION: X is Sar

<400> SEQUENCE: 3

Xaa Met Xaa Arg Leu Arg Xaa Cys

```
1               5

<210> SEQ ID NO 4
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X is (D)-Cys
<220> FEATURE:
<221> NAME/KEY: MISC_FEATURE
<222> LOCATION: (3)..(3)
<223> OTHER INFORMATION: X is Pip
<220> FEATURE:
<221> NAME/KEY: MISC_FEATURE
<222> LOCATION: (8)..(8)
<223> OTHER INFORMATION: X is Pen

<400> SEQUENCE: 4

Xaa Met Xaa Arg Leu Arg Gly Xaa
1               5

<210> SEQ ID NO 5
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X is (D)-Cys
<220> FEATURE:
<221> NAME/KEY: MISC_FEATURE
<222> LOCATION: (3)..(3)
<223> OTHER INFORMATION: X is Pip
<220> FEATURE:
<221> NAME/KEY: MISC_FEATURE
<222> LOCATION: (7)..(7)
<223> OTHER INFORMATION: X is Sar
<220> FEATURE:
<221> NAME/KEY: MISC_FEATURE
<222> LOCATION: (8)..(8)
<223> OTHER INFORMATION: X is Pen

<400> SEQUENCE: 5

Xaa Met Xaa Arg Leu Arg Xaa Xaa
1               5

<210> SEQ ID NO 6
<211> LENGTH: 8
<212> TYPE: PRT
<213> ORGANISM: Artificial Sequence
<220> FEATURE:
<223> OTHER INFORMATION: peptide

<400> SEQUENCE: 6

Cys Met Pro Arg Leu Arg Gly Cys
1               5

<210> SEQ ID NO 7
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
```

```
<223> OTHER INFORMATION: X is (D)-Cys

<400> SEQUENCE: 7

Xaa Met Pro Arg Leu Arg Gly Cys
1               5

<210> SEQ ID NO 8
<211> LENGTH: 15
<212> TYPE: PRT
<213> ORGANISM: Artificial Sequence
<220> FEATURE:
<223> OTHER INFORMATION: peptide

<400> SEQUENCE: 8

Asp Ser Gly Leu Cys Met Pro Arg Leu Arg Gly Cys Asp Pro Arg
1               5                   10                  15

<210> SEQ ID NO 9
<211> LENGTH: 8
<212> TYPE: PRT
<213> ORGANISM: Artificial Sequence
<220> FEATURE:
<223> OTHER INFORMATION: peptide
<220> FEATURE:
<221> NAME/KEY: MISC_FEATURE
<222> LOCATION: (1)..(1)
<223> OTHER INFORMATION: X is (D)-Pen
<220> FEATURE:
<221> NAME/KEY: MISC_FEATURE
<222> LOCATION: (3)..(3)
<223> OTHER INFORMATION: X is Thz

<400> SEQUENCE: 9

Xaa Met Xaa Arg Leu Arg Gly Cys
1               5

<210> SEQ ID NO 10
<211> LENGTH: 20
<212> TYPE: DNA
<213> ORGANISM: Artificial Sequence
<220> FEATURE:
<223> OTHER INFORMATION: forward primer

<400> SEQUENCE: 10
cttggcatta tgcacctcca                                              20

<210> SEQ ID NO 11
<211> LENGTH: 67
<212> TYPE: DNA
<213> ORGANISM: Artificial Sequence
<220> FEATURE:
<223> OTHER INFORMATION: reverse primer C

<400> SEQUENCE: 11
ctggccagct agcactcagc aaccgcgaag acgaggcata caagcacctt tacccggaga   60
cagggag                                                            67

<210> SEQ ID NO 12
<211> LENGTH: 66
<212> TYPE: DNA
<213> ORGANISM: Artificial Sequence
<220> FEATURE:
<223> OTHER INFORMATION: reverse primer D

<400> SEQUENCE: 12
ctggccagct agcactcgca gggtctgccc agcattctgc aagcaccttt acccggagac   60
```

```
agggag                                                           66

<210> SEQ ID NO 13
<211> LENGTH: 8
<212> TYPE: PRT
<213> ORGANISM: Artificial Sequence
<220> FEATURE:
<223> OTHER INFORMATION: peptide scramble
<220> FEATURE:
<221> NAME/KEY: MISC_FEATURE
<222> LOCATION: (1)..(1)
<223> OTHER INFORMATION: X is (D)-Cys

<400> SEQUENCE: 13

Xaa Arg Pro Leu Gly Arg Met Cys
1               5

<210> SEQ ID NO 14
<211> LENGTH: 8
<212> TYPE: PRT
<213> ORGANISM: Artificial Sequence
<220> FEATURE:
<223> OTHER INFORMATION: peptide scramble

<400> SEQUENCE: 14

Cys Arg Met Leu Gly Arg Pro Cys
1               5

<210> SEQ ID NO 15
<211> LENGTH: 5
<212> TYPE: PRT
<213> ORGANISM: Artificial sequence
<220> FEATURE:
<223> OTHER INFORMATION: spacer

<400> SEQUENCE: 15

Gly Gly Gly Gly Ser
1               5

<210> SEQ ID NO 16
<211> LENGTH: 6
<212> TYPE: PRT
<213> ORGANISM: Artificial sequence
<220> FEATURE:
<223> OTHER INFORMATION: spacer

<400> SEQUENCE: 16

Gly Gly Gly Arg Asp Asn
1               5
```

COMPOSITIONS AND METHODS FOR CANCER IMAGING AND RADIOTHERAPY

CROSS-REFERENCE TO RELATED APPLICATION

This application is the U.S. national stage application of International Patent Application No. PCT/EP2018/052234, filed Jan. 30, 2018.

The Sequence Listing for this application is labeled "Seq-List-replace.txt" which was created Jan. 24, 2023 and is 4,721 bytes. The entire content of the sequence listing is incorporated herein by reference in its entirety.

FIELD OF THE INVENTION

The invention relates to compositions and methods for cancer imaging, detection and radiotherapy. The invention particularly relates to conjugated compounds containing a LDLR-targeting peptide and a pharmaceutically acceptable marker, as well as to the use thereof for labelling, detecting, staging or treating cancers, particularly cancers which overexpress the Low-Density Lipoprotein Receptor (LDLR).

BACKGROUND OF THE INVENTION

Cancers figure among the leading causes of morbidity and mortality worldwide, with approximately 14 million new cases and 8.2 million cancer related deaths in 2012 according to Cancer Research UK and WHO.

While many forms of cancer can now be treated, some of them remain difficult to treat. For example, pancreatic cancer remains one of the deadliest, with a 75% mortality rate within the first year and only a 6% 5-year survival. Almost 12,000 individuals are diagnosed with pancreatic cancer every year in France and about 340,000 in the world. This cancer is expected to become the second cause of cancer death by 2030. Pancreatic cancer affects both men and women over 50 years of age and is particularly difficult to treat. Similarly, glioblastoma multiforme (GBM), the most common and most aggressive malignant primary brain tumour, is a rare though life-threatening disease. Each year, about 25,000 new cases are diagnosed in the European Union (see Worldwide Website: pubcan.org/cancer). It remains an important clinical challenge since it does not respond well to current treatments. Indeed, today the survival after 5 years is about 3% and despite significant advances in our basic understanding of tumour pathogenesis, the median overall survival of patients has increased only 3.3 months (from 11.3 months to 14.6 months) over the past 25 years (Patel M A, et al. 2014 Sep. 29; 6(4):1953-85).

Most of the deaths observed in cancers could be avoided if an early diagnosis is achieved. Given that five-year survival rates for various cancers drastically plummet with tumor stage at the time of detection, there is a pressing need to develop non-invasive imaging tools capable of identifying tumors at the earliest possible time and to identify patients likely to respond to therapeutic interventions. Cancer mortality and morbidity can be greatly improved by the development of effective imaging and therapeutic agents.

Many efforts have been made to develop new methods for an early and accurate diagnosis of cancer. Various imaging techniques are used including positron emission tomography (PET scan), single photon computed tomography (SPECT), X-ray computed tomography (CT scan), nuclear scan, ultrasound, and magnetic resonance imagery (MRI). Although these imaging technologies are well developed, they rely mostly on nonspecific, macroscopic and physiological changes of the organ analyzed. By far the most widely used PET tracer in oncology is $^{18}$F-FDG, a probe that measures glucose utilization and established tool for cancer diagnosis and staging. However, $^{18}$F-FDG has important limitations, including modest uptake in some tumors (e.g. prostate) and elevated background uptake in certain normal tissues (e.g. brain).

Selective receptor-targeting peptide based agents have attracted considerable attention in molecular imaging of tumor cells that overexpress corresponding peptide receptors due to their unique properties such as high affinities and specificities for their targets. Indeed, targeting a receptor which is highly expressed in the tumor should provide a better cancer diagnosis since the receptor-targeting peptide will differentiate pathological from normal tissue.

Regarding cancer treatment, many approaches have been used, alone or in combination, such as chemotherapy, immunotherapy, or radiation therapy.

Radiation therapy (also called radiotherapy, X-ray therapy, or irradiation) is based on the use of ionizing radiation to kill cancer cells and shrink tumors. It is used on a wide variety of tumors for both curative and palliative indications. The effects of radiation therapy are localized and confined to the region being treated. Radiation therapy causes injury or destroys cells in the area being treated (the "target tissue") by damaging their genetic material, making it impossible for these cells to continue to grow and divide. Although radiation damages both cancer cells and normal cells, most normal cells can recover from the effects of radiation and function properly. The goal of radiation therapy is to damage as many cancer cells as possible, while limiting harm to nearby healthy tissue. Ionizing radiation works by damaging the DNA of cancerous tissue leading to cellular death.

There are several types of radiation therapy among which:

External Beam Radiotherapy (EBRT) which is the most common form of radiotherapy. The patient sits or lies on a couch and an external source of ionizing radiation is pointed at a particular part of the body. X-rays and electron beams are the most widely used sources for external beam radiotherapy.

Brachytherapy in which a sealed radiation source is placed inside or next to the area requiring treatment.

Unsealed source radiotherapy (or unsealed source radionuclide therapy) uses solid, liquid, gaseous or other forms of radioactive substances called radiopharmaceuticals (essentially a radioactive drug). These are introduced into the body by various means (injection or ingestion mainly) and localize to specific locations, organs or tissues depending on their properties and administration routes. This includes anything from a simple compound such as sodium iodide that locates to the thyroid via trapping the iodide ion, to complex biopharmaceuticals such as recombinant antibodies which are attached to radionuclides and seek out specific antigens on cell surfaces. This technique is based on the physical, chemical and biological properties of the radiopharmaceutical to target areas of the body for radiation treatment.

Radiotherapy presents several side effects. The nature, severity, and longevity of side effects depends on the organs that receive the radiation, the treatment itself (type of radiation, dose, fractionation, concurrent chemotherapy), and the status of the patient. There are acute side effects (nausea, vomiting, intestinal discomfort, swelling, infertility . . . ) and late side effects (fibrosis, hair loss, dryness, heart disease, cognitive decline . . . ). Therefore, there is a need to develop targeted radiotherapy which will induce fewer side effects.

Peptide receptor radionuclide therapy (PRRT) is a molecular therapy (also called radioisotope therapy) used to treat certain cancers such as neuroendocrine carcinoma. In PRRT, a cell-targeting protein (or peptide) is combined with a small amount of radioactive material, or radionuclide, creating a special type of radiopharmaceutical called a radiopeptide. When injected into the patient's bloodstream, this radiopeptide travels and binds to specific tumor cells, delivering a high dose of radiation to the cancer tissue while preserving normal tissue.

There are clearly unmet medical needs in the field of effective imaging and targeting agents. Targeting a receptor which is highly expressed in the tumor should provide better cancer diagnosis and therapy since the receptor-targeting peptide will differentiate pathological from normal tissue.

The present application relates to novel compositions and methods for cancer imaging and radiotherapy based on LDLR-targeting agents. The invention provides conjugated compounds that bind LDLR and are optimized for addressing imaging or radiotherapy agents, and shows such compounds allow effective, reliable and selective labelling of LDLR-overexpressing cancer cells, and are most suitable for efficient diagnosis or radiotherapy of such cancers.

SUMMARY OF THE INVENTION

The present invention provides new compositions and methods for effective imaging, diagnosis, detection or radiotherapy of LDLR-expressing cancers. The invention particularly provides conjugate compounds capable of binding to and imaging LDLR-overexpressing cancer cells. The invention allows detection of such cancers in vivo, as well as effective and selective radiotherapy thereof. The invention indeed shows the conjugated agents of the invention are able to discriminate between cancer and non-cancer cells, and may be used to provide sufficient level of irradiation to cancer cells, while not affecting healthy tissues.

One object of the invention thus relates to a conjugated compound of formula (I):

wherein,
M represents a pharmaceutically acceptable marker, and
P represents a peptide or pseudo-peptide having at most 30 amino acid residues and able to bind the LDLR,
for use in a method of labelling and/or detecting cancerous cells in a subject by administration of the conjugated compound to the subject and analysis of the presence and/or the amount of marker.

A further object of the invention is a method for labelling or detecting a LDLR-overexpressing cancer in a subject, comprising (i) administering to the subject a compound of formula (I):

wherein,
M represents a pharmaceutically acceptable marker, and
P represents a peptide or pseudo-peptide having at most 30 amino acid residues and able to bind the LDLR,
and (ii) analysing the presence and/or the amount of marker.

In a particular embodiment, the conjugated compound is a multimeric compound comprising several monomers of formula (I).

According to preferred embodiments M represents a radionuclide or a fluorescent marker, and P comprises the amino acid sequence (II):

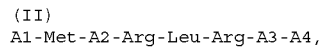

wherein A1 and A4 independently represent a cysteine or an analogue or isostere thereof, A2 represents a proline or an analogue or isostere thereof, and A3 represents a glycine or an analogue or isostere thereof.

Furthermore, M and P may be linked to each other either directly or by a spacer, either covalently or through non-covalent interaction. In a particular embodiment, M is linked to P using a prosthetic group or is encaged using a chelating group such as a NODAGA, DOTA, DOTA-GA or NOTA, or functional derivatives thereof.

Another object of the invention relates to a conjugated compound of formula (III):

wherein,
M represents a pharmaceutically acceptable radionuclide,
C represents a chelator which forms a chelate with M,
S represents a spacer, and
P represents a peptide or pseudo-peptide having at most 30 amino acid residues and able to bind the LDLR.

A further object of the invention relates to a composition comprising a conjugated compound as described above, as well as the uses thereof in medical imaging or radiotherapy.

A further object of the invention is a method for treating a LDLR-overexpressing cancer in a subject, comprising administering to the subject a conjugated compound of formula (III):

wherein,
M represents a pharmaceutically acceptable radionuclide suitable for use in radiotherapy,
C represents a chelator which forms a chelate with M,
S represents a spacer, and
P represents a peptide or pseudo-peptide having at most 30 amino acid residues and able to bind the LDLR.

The invention may be used to detect or treat any LDLR-overexpressing cancer, such as pancreatic, adrenal, glioblastoma, prostate, colon, liver, pancreas, ovaries, lung or stomach cancers. It may be used in any mammal, such as human subjects.

BRIEF DESCRIPTION OF FIGURES

FIG. 1: Western Blot showing human and mouse LDLR expression in various cancer cells lines: (A) CHO95 (a cell line that over-expresses human LDLR in fusion with eGFP), Hela (Cervix Cancer), NCI-H295R (Adrenal Gland Adenocarcinoma), Capan, BxPC3 and Panc1 (Pancreatic Cancer), MCF-7 and MDA-MB231 (Breast Cancer). On the right panel, the expression of LDLR in a mouse pancreatic cell line PK4 is compared to a mouse normal pancreas. (B). The glioblastoma cell line U87MG (two lanes), prostate cancer cell line PC3 and NCI-H295R are represented.

FIG. 2: Binding/endocytosis of conjugate A (A), conjugate B (B), conjugate C (C) and conjugate D (D) on CHO cells expressing human LDLR coupled to GFP. The LDLR-GFP signal is visualizable in column 2, the conjugate signal is either directly visualized in column 4 using the A680 fluorescence or in column 3 using an anti-hFc-A594 conjugated secondary antibody. Cell nuclei were stained in blue with Hoechst and its signal can be visualized in column 1. The co-labelling of LDLR-GFP and conjugates can be visualized as a highlight signal in column 5 on the merge image.

FIG. 7: PET imaging of mice administered with $^{68}$Ga-CH44 (A) and $^{68}$Ga-CH40 (B) at day 32 after implantation with NCI-H295R cells. The adrenal tumour is indicated by a circle.

FIG. 8: PET imaging of mice administered with $^{68}$Ga-FG770 (A) and $^{68}$Ga-FG769 (B) at day 37 after implantation with NCI-H295R cells.

FIG. 13: PET imaging of mice administered with $^{68}$Ga-CH44 (A) and $^{68}$Ga-MG04 (B) at day 48 after implantation with NCI-H295R cells.

DETAILED DESCRIPTION OF THE INVENTION

Figure 3:
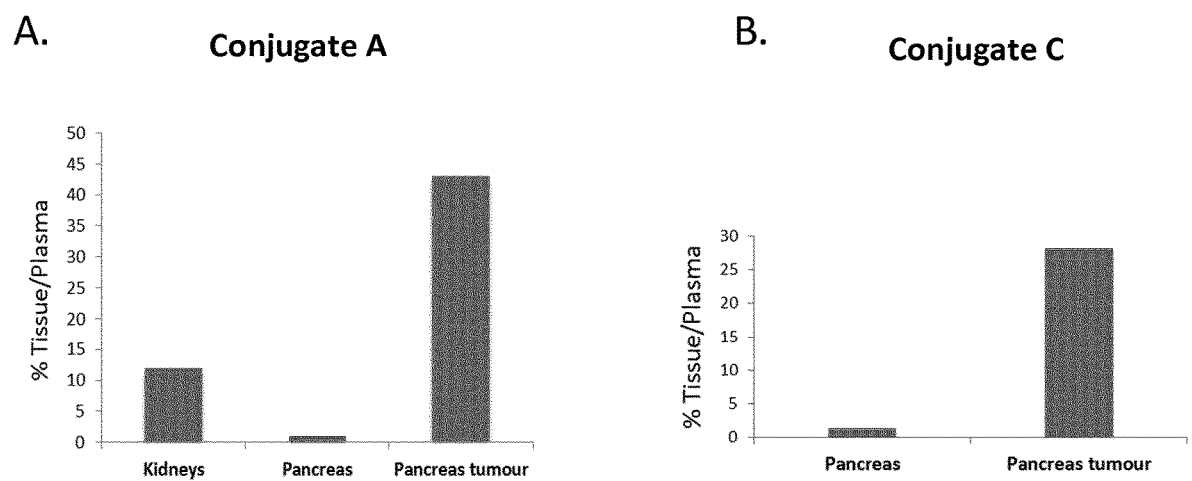
FIG. 3: In A, tissue biodistribution of conjugate A in pancreas, pancreas tumour and kidney (control) in mice implanted with PK4A tumour and injected in the tail vein with conjugate A. In B, tissue biodistribution of conjugate C in pancreas and pancreas tumour in mice injected with conjugate C. Biodistribution was assessed using ELISA quantification.

The invention relates to compositions and methods for cancer imaging and radiotherapy based on LDLR-targeting agents. The invention provides conjugate compounds comprising a LDLR-binding moiety and a pharmaceutically acceptable marker. The invention more particularly shows such compounds can effectively label cancer cells in vitro and in vivo and allow efficient imaging, detection, staging or radiotherapy thereof.

More specifically, an object of the invention resides in a method of labelling cancers or tumors or cancer/tumor cells using a conjugate compound of formula (I):

$$M\text{-}P \qquad (I),$$

wherein,
M represents a pharmaceutically acceptable marker, and
P represents a peptide or pseudo-peptide having at most 30 amino acid residues and able to bind the Low-Density Lipoprotein Receptor (LDLR).

Human LDLR is a transmembrane protein of 839 amino acids comprising three regions: the extracellular region (1-768), the transmembrane region (768-790) and the cytoplasmic region (790-839). The extracellular region is divided into two subregions: that of LDL binding (1-322) and that outside the LDL binding region (322-768). LDLR is reported to be expressed by most nucleated cells and it is generally accepted that 1000 to 3000 LDLR are present at the surface of a non-pathological cells. The amount of LDLR on cancer cells may increase drastically, up to 100,000 or more. Tumor cells which have been reported to overexpress LDLR include cells of prostate cancer (Chen et al., 2001, Int. J. Cancer, 91, 41-45), colon cancer (Niendorf et al., 1995, Int. J. Cancer, 61, 461-464), leukemia (Tatidis et al., 2002, Biochem. Pharmacol., 63, 2169-2180), colorectal cancer (Caruso et al., 2001, Anticancer Res., 21, 429-433), breast cancer (Graziani et al., 2002, Gynecol. Oncol., 85, 493-497), glioblastoma brain tumor cells (Malentiska et al., 2000, Cancer Res., 60, 2300-2303; Nikanjam et al., 2007, Int. J. Pharm., 328, 86-94), as well as cells of liver, pancreas, ovaries, lung and stomach cancers. It is, however, not known whether such increased expression can affect conformation/availability of the receptor, particularly the extracellular region 322-768. Indeed, it has been observed that high expression of receptors can lead to aggregation or conformational changes. Such aggregation may alter the capacity to target agents to such cells using LDLR-targeting agents that bind the extracellular region 322-768.

Interestingly, and despite ubiquitous expression of LDLR, the conjugates of the invention allow effective labelling of cells that overexpress LDLR, particularly of cancerous cells overexpressing LDLR, and enable effective targeting of such LDLR-expressing cancerous cells. Such an effect may be due to appropriate receptor density, conjugate binding affinity for LDLR and mechanism of action (noncompetitive).

The invention shows that conjugates of the invention retain the capacity to effectively bind LDLR-overexpressing cancer cells.

The invention shows that the conjugates of the invention can direct pharmaceutically acceptable markers to LDLR-overexpressing cells in a manner suitable for discriminating such cells (e.g. cancer cells) from cells having regular levels of LDLR (e.g. normal tissue).

The invention shows the conjugates of the invention can confer sufficient level of labelling to LDLR-overexpressing cells, despite LDLR density and possible reorganization.

The invention thus provides safe and effective labelling and radiotherapy agents and allows design of effective cancer diagnosis and therapeutic methods.

An object of the invention thus relates to a conjugated compound of formula (I):

$$M\text{-}P \qquad (I),$$

wherein,
M represents a pharmaceutically acceptable marker, and
P represents a peptide or pseudo-peptide having at most 30 amino acid residues and able to bind LDLR, for use in a method of labelling and/or detecting cancerous cells in a subject by administration of the conjugated compound to the subject and analysis of the presence and/or the amount of marker.

The invention also relates to a method for labelling, imaging, diagnosing or staging cancer in a subject using a conjugate compound as defined above.

In a particular embodiment, the conjugated compounds of the invention further comprise a second targeting group T that binds to a molecule distinct from LDLR. Examples of such dual conjugated compounds are compounds of formula (IV) below:

$$M_n\text{-}P\text{-}T\text{-}M_m \quad (IV),$$

wherein, M and P are as defined above, T represents a second targeting group, n is 1 or 0, m is 1 or 0. Preferably, m+n=1.

In a further particular embodiment, the dual conjugated compounds have the following structure:

$$(M\text{-}C\text{-})_n P\text{-}T(\text{-}C\text{-}M)_m$$

wherein, M, C and P are as defined above, T represents a second targeting group, n is 1 or 0, m is 1 or 0. Preferably, m+n=1.

T may be any group that binds to a target molecule distinct from LDLR (or to a cell expressing such molecule). Preferably, such target molecule is a molecule expressed by cancer cells, such as by pancreas cancer cells or prostate cancer cells or ovarian cancer cells or adrenal cancer cells. Examples of such targeting group include, without limitation, PSMA (prostate specific membrane antigen), neurotensin, analogues of somatostatin, as well as derivatives thereof.

Conjugates

The present invention discloses the use of particular LDLR-targeting conjugates, as well as the design of novel conjugates. Such conjugates may be monomers of formula (I), or multimeric structures, as will be described below.

In a particular embodiment, the conjugates are compounds of formula M-P (I) as defined above. Preferably, P comprises the amino acid sequence (II):

$$\text{(II)}$$
$$A1\text{-}Met\text{-}A2\text{-}Arg\text{-}Leu\text{-}Arg\text{-}A3\text{-}A4,$$

wherein A1 and A4 independently represent a cysteine or an analogue thereof or an isostere thereof, A2 represents a proline or an analogue thereof or an isostere thereof, and A3 represents a glycine or an analogue thereof or an isostere thereof.

More particularly, A1 and A4 represent, independently from each other, an amino acid residue selected from cysteine (Cys, C), of D or L configuration, or a derivative thereof selected from 2-amino-3-mercaptopropanoic acid and S-substituted derivatives thereof, S-acetylcysteine or 2-amino-3-(acetylthio)propanoic acid, selenocysteine (Sec, U) or 2-amino-3-(seleno)propanoic acid, cysteinol, 3-mercaptopropanoic acid (Mpa), or penicillamine (Pen), of L or D configuration.

In a preferred embodiment, A1 and A4 are selected, independently from each other, from cysteine (Cys), (D)-cys, penicillamine (Pen) and (D)-penicillamine ((D)-Pen).

A2 represents more preferentially a residue selected from proline (Pro, P), pyrolidine-2-carboxylic acid, homoproline, 2-(2-pyrrolidinyl)ethanoic acid, 3-hydroxyproline (3Hyp), 4-hydroxyproline (4Hyp), 3-methylproline, 3,4-dehydroproline, 3,4-methanoproline, 4-aminoproline, 4-oxoproline, thioproline, thiazolidine-4-carboxylic acid (Thz), 2-oxothiazolidine-4-carboxylic acid, indolin-2-carboxylic acid (Idc), pipecolic acid (Pip), piperidin-2-carboxylic acid, nipecotic acid (Nip), piperidin-3-carboxylic acid, 4-oxopipecolic acid, 4-hydroxypipecolic acid, amino-1-cyclohexanecarboxylic acid, or prolinol.

In a preferred embodiment, A2 is selected from proline, pipecolic acid (Pip) or thiazolidine-4-carboxylic acid (Thz).

A3 represents more preferentially a residue selected from glycine (Gly, G), 2-aminoethanoic acid, sarcosine (Sar), N-methylglycine (MeGly), N-ethylglycine (EtGly), allylglycine (allylGly), 2-aminopent-4-enoic acid, 2-cyclopentylglycine (Cpg), 2-cyclohexylglycine (Chg), 2,2-dipropylglycine (Dpg), 2-(3-indolyl)glycine (IndGly), 2-indanylglycine (Igl), 2-neopentylglycine (NptGly), 2-octylglycine (OctGly), 2-propargylglycine (Pra) or 2-amino pent-4-ynoic acid, 2-phenylglycine (Phg), 2-(4-chlorophenyl)glycine, azaglycine (AzGly), glycinol or 2-aminoethanol.

In a preferred embodiment, A3 is glycine or sarcosine.

In a preferred embodiment, P comprises or consists essentially or consists of an amino acid sequence selected from any one of SEQ ID NO: 1 to SEQ ID NO: 9 below:

```
                                                 SEQ ID NO: 1
(D)-Cys-Met-Thz-Arg-Leu-Arg-Gly-Pen;,

SEQ ID NO: 2
(D)-Cys-Met-Thz-Arg-Leu-Arg-Sar-Pen;,

SEQ ID NO: 3
(D)-Cys-Met-Pip-Arg-Leu-Arg-Sar-Cys;,

SEQ ID NO: 4
(D)-Cys-Met-Pip-Arg-Leu-Arg-Gly-Pen;,

SEQ ID NO: 5
(D)-Cys-Met-Pip-Arg-Leu-Arg-Sar-Pen;,

SEQ ID NO: 6
Cys-Met-Pro-Arg-Leu-Arg-Gly-Cys;,

SEQ ID NO: 7
(D)-Cys-Met-Pro-Arg-Leu-Arg-Gly-Cys;,

SEQ ID NO: 8
Asp-Ser-Gly-Leu-Cys-Met-Pro-Arg-Leu-Arg-Gly-Cys-
Asp-Pro-Arg;,

SEQ ID NO: 9
(D)-Pen-Met-Thz-Arg-Leu-Arg-Gly-Cys.,
```

Results obtained by the inventors show that the conjugates of the invention have an improved affinity ($K_D$) for LDLR compared to a scrambled peptide which comprises the amino acid sequence of SEQ ID NO: 13 or SEQ ID NO: 14 (Cys-Arg-Met-Leu-Gly-Arg-Pro-Cys) (see Example 3). Moreover, the conjugates of the invention present a better accumulation in pancreatic tumour compared to healthy pancreas (see Example 4). In particular, as shown in the examples, the labelling of cancer tissue can be 10- to 50-fold superior to the labelling of non-cancer tissue. This level of accumulation is well sufficient to allow a reliable and clear discrimination in imagery. Furthermore, it means that, in case of a use in radiotherapy, the conjugate has a very good specificity for tumour cells compared to healthy cells.

As discussed above, the marker M can be any radionuclide or fluorescent marker.

Fluorescent markers which may be used are for example Alexa Fluor 680, CF680, ATTO680, Fluoroprobes682, Cyanine 5.5, IRDye 680, or Vivotag. In a general manner, all near infra-red (IR) fluorescent markers may be used for imaging as they permit minimal tissue auto-fluorescence. More specifically, Alexa Fluor 680 is a bright and photo-stable near-IR dye that is spectrally similar to the Cy5.5 dye. Used for stable signal generation in imaging and flow cytometry, Alexa Fluor 680 dye is water soluble and pH-insensitive from pH 4 to pH 10. The NHS ester (or succinimidyl ester) of Alexa Fluor 680 is the most popular tool for conjugating this dye to a protein or an antibody. NHS ester of dyes can be used to label primary amines (R—$NH_2$) of proteins, amine-modified oligonucleotides, and other amine-containing molecules.

In a most preferred embodiment, M is a radionuclide adapted for use in medical imagery, for example for use in positron emission tomography (PET) imagery, scintigraphy, positron emission tomography-computed tomography or single photon emission computed tomography. Preferably, M is a radionuclide adapted for use in PET.

Examples of radionuclides suitable for use in the present invention include, without limitation, $^{18}F$, $^{11}C$, $^{15}O$, $^{13}N$, $^{68}Ga$, $^{82}Rb$, and $^{89}Zr$. Preferred radionuclides for use in imagery shall have a short half-life (e.g., from 30 minutes to 3 or 4 days) and low energy emission (e.g., inferior to 300 keV gamma-emitting radionuclides). Preferably, the radionuclide is $^{68}Ga$. $^{68}Ga$ has a short half-life (68 minutes) and is a positron-emitting isotope.

For use in radiotherapy, radionuclides are typically beta- or high energy gamma-emitting radionuclides, preferably with a longer half-life (e.g., between 1 to 75 days). Preferred radionuclides for use in radiotherapy are selected from $^{90}Y$, $^{111}In$, $^{131}I$, and $^{177}Lu$. In a preferred embodiment, $^{90}Y$, $^{177}Lu$ or $^{111}In$ are used.

The conjugates of the invention can be synthesized by any technique known to the skilled in the art (chemical, biological or genetic synthesis, etc.). For chemical syntheses, commercial apparatuses that can incorporate natural as well as non-natural amino acids, such as D enantiomers and residues with side chains with hydrophobicities and steric obstructions different from those of their natural homologues (so-called exotic, i.e., non-coded, amino acids), or a peptide sequence containing one or more peptidomimetic bonds that can include notably intercalation of a methylene (—$CH_2$—) or phosphate (—$PO_2$—) group, a secondary amine (—NH—) or an oxygen (—O—) or an N-alkylpeptide, are used. The peptides or pseudo-peptides, or a proteic part thereof, can also be obtained from a nucleic acid sequence coding for the same. These nucleic acid sequences can be DNA or RNA and be combined with control sequences and/or be inserted in biological expression vectors.

In the conjugate compounds of the invention, coupling between M and P (and/or between P and T) can be carried out by any acceptable means of bonding taking into account the chemical nature, obstruction and number of associated agents. Coupling can thus be carried out by one or more covalent, ionic, hydrogen, hydrophobic or Van der Waals bonds. Also, coupling can be carried out at any site of the peptide or pseudo-peptide where functional groups such as —OH, —SH, —$CO_2H$, —$NH_2$, —$SO_3H$, —CN, —$N_3$, —NCS, —$PO_2H$, alkyne, maleimide or succinimide ester are naturally present or have been introduced. Thus, M can be linked (coupled) to the peptide or pseudo-peptide by a covalent bond either at the N-term or C-term ends, at the reactive groups carried by the natural or non-natural amino acid side chains of this peptide sequence, or through a prosthetic group. Similarly, coupling can be carried out at any site of the imaging or radiotherapeutic agent.

It is preferable that the interaction is sufficiently strong so that M is not dissociated from the peptide before having reached its site of action, and that M and the peptide stay coupled during the time necessary for performing an imaging method or for M to have a therapeutic effect. For this reason, the preferred coupling of the invention is covalent or ionic bounding. The imaging or radiotherapeutic agent can be coupled directly to the peptide either at one of its terminal ends (N-term or C-term), or at a side chain of one of the constitutive amino acids of the sequence. The imaging or radiotherapeutic agent can also be coupled indirectly by means of a linker or spacer, either at one of the terminal ends of the peptides, or at a side chain of one of the constitutive amino acids of the sequence. In a particular embodiment, M is linked to the peptide by encaging using e.g., a chelating agent.

In this regard, in a preferred embodiment, the conjugated compound comprises a chelator C able to form a chelate with M. Such conjugates have a structure M-C—P. Various chelators may be used. Preferably, C is selected from NODAGA (1,4,7-triazacyclononane-1-glutaric acid-4,7-diacetic acid), DOTA (tetraazacyclododecane-1,4,7,10-tetraacetic acid), NOTA (1,4,7-triazacyclononane-triacetic acid), DOTA-GA (2,2',2"-(10-(2,6-dioxotetrahydro-2H-pyran-3-yl)-1,4,7,10-tetraazacyclododecane-1,4,7 triyl) triacetic acid), and functional derivatives thereof. NODAGA and NOTA are preferred for imaging, while DOTA is preferred for radiotherapy.

The term "functional derivatives" means any compound derived from the above-mentioned chelators by replacement of one or more of the functional groups thereof (i.e. groups involved in the chelating function) by another functional group without prejudice on said chelating function, and/or by addition and/or deletion of groups not involved in the chelating function without prejudice on said chelating function.

The chelator C may be linked directly to the peptide P (or to T), or through a spacer S, typically covalently coupled to P and C (or to T and C). In this regard, in a particular embodiment, the conjugates comprise the structure M-C—P wherein M, C and P are as defined above and wherein C is linked directly to the peptide P. In another particular embodiment, the conjugates comprise the structure M-C—S—P, wherein M, C, S, and P are as defined above. In a further particular embodiment, the conjugates comprise the structure M-C—P-T or P-T-C-M or M-C—S—P-T or P-T-S—C-M, wherein M, C, S, P and T are as defined above. In a further embodiment, P and T are coupled through az spacer group.

S may be selected from bi- or multifunctional agents of alkyl, aryl, PEG or peptidic nature, and having at their extremities functional groups such as amines, esters, aldehydes, alkyl or aryl acids, anhydride, sulfhydryl or carboxyl groups, groups derived from cyanogen bromide or chloride, carbonyldiimidazole, succinimide esters, sulfonic halides, maleimides, azide, isothiocyanate, alkynes. In a particular embodiment, S comprises one or several PEG, preferably with a beta-Alanine at one end thereof. For example, S is an oligomer of twelve PEG with a beta-Alanine at one end of the chain. In another embodiment, S comprises several Gly residues, such as G3 or G4S (SEQ ID NO: 15). In other particular embodiments, S comprises hydrophilic negatively charged peptide sequences encompassing amino acids of D or L configuration such as several His-Glu repetitive units (2 or 3 units) or hydrophilic neutral sequences encompassing amino acids of D or L configuration such as Gly-Gly-Gly-Arg-Asp-Asn (SEQ ID NO: 16). In another embodiment, metabolizable groups stable in plasma but specifically cleaved in the kidneys by hydrolases at the proximal tubular brush border membrane can be used to reduce the kidney retention. For example a glycyl-lysine bond can be used. S may thus be any pharmacokinetic modifier.

In a particular embodiment, the invention relates to conjugated compounds of formula (III):

M-C—S—P  (III), wherein,
M represents a pharmaceutically acceptable radionuclide,
C represents a chelator which forms a chelate with M,
S represents a spacer, and
P represents a peptide or pseudo-peptide having at most 30 amino acid residues and able to bind the Low-Density Lipoprotein Receptor (LDLR).

In a particular embodiment, the invention relates to conjugated compounds as defined above which further comprise a second targeting group T.

Preferred conjugated compounds of the invention are compounds of formula (III) wherein
M represents a pharmaceutically acceptable radionuclide,
C is selected from NODAGA, DOTA, NOTA, and DOTA-GA,
S represents a spacer comprising a bifunctional agent, PEG or a peptide, or S is absent, and
P represents a peptide or pseudo-peptide having at most 30 amino acid residues and able to bind the Low-Density Lipoprotein Receptor (LDLR).

In most preferred compounds of the invention, C is NODAGA or DOTA and P comprises an amino acid sequence selected from SEQ ID NO: 1-9.

Specific examples of conjugated compounds of the invention include:

| | |
|---|---|
| $^{68}$Ga-NODAGA-, | SEQ ID NO: 1 |
| $^{68}$Ga-NOTA-, | SEQ ID NO: 1 |
| $^{68}$Ga-DOTA-, | SEQ ID NO: 1 |
| $^{68}$Ga-DOTA-GA-, | SEQ ID NO: 1 |
| $^{18}$F-NODAGA-, | SEQ ID NO: 1 |
| $^{18}$F-NOTA-, | SEQ ID NO: 1 |
| $^{18}$F-DOTA-, | SEQ ID NO: 1 |
| $^{18}$F-DOTA-GA-, | SEQ ID NO: 1 |
| $^{90}$Y-NODAGA-, | SEQ ID NO: 1 |
| $^{90}$Y-NOTA-, | SEQ ID NO: 1 |
| $^{90}$Y-DOTA-, | SEQ ID NO: 1 |
| $^{90}$Y-DOTA-GA-, | SEQ ID NO: 1 |
| $^{111}$In-NODAGA-, | SEQ ID NO: 1 |
| $^{111}$In-NOTA-, | SEQ ID NO: 1 |
| $^{111}$In-DOTA-, | SEQ ID NO: 1 |
| $^{111}$In-DOTA-GA-, | SEQ ID NO: 1 |
| $^{177}$Lu-NODAGA-, | SEQ ID NO: 1 |
| $^{177}$Lu-NOTA-, | SEQ ID NO: 1 |
| $^{177}$Lu-DOTA-, | SEQ ID NO: 1 |
| $^{177}$Lu-DOTA-GA-, | SEQ ID NO: 1 |
| $^{68}$Ga-NODAGA-, | SEQ ID NO: 2 |
| $^{68}$Ga-NOTA-, | SEQ ID NO: 2 |
| $^{68}$Ga-DOTA-, | SEQ ID NO: 2 |
| $^{68}$Ga-DOTA-GA-, | SEQ ID NO: 2 |
| $^{18}$F-NODAGA-, | SEQ ID NO: 2 |
| $^{18}$F-NOTA-, | SEQ ID NO: 2 |
| $^{18}$F-DOTA-, | SEQ ID NO: 2 |
| $^{18}$F-DOTA-GA-, | SEQ ID NO: 2 |
| $^{90}$Y-NODAGA-, | SEQ ID NO: 2 |
| $^{90}$Y-NOTA-, | SEQ ID NO: 2 |
| $^{90}$Y-DOTA-, | SEQ ID NO: 2 |
| $^{90}$Y-DOTA-GA-, | SEQ ID NO: 2 |
| $^{111}$In-NODAGA-, | SEQ ID NO: 2 |
| $^{111}$In-NOTA-, | SEQ ID NO: 2 |
| $^{111}$In-DOTA-, | SEQ ID NO: 2 |
| $^{111}$In-DOTA-GA-, | SEQ ID NO: 2 |
| $^{177}$Lu-NODAGA-, | SEQ ID NO: 2 |
| $^{177}$Lu-NOTA-, | SEQ ID NO: 2 |
| $^{177}$Lu-DOTA-, | SEQ ID NO: 2 |

-continued

| | |
|---|---|
| $^{177}$Lu-DOTA-GA-, | SEQ ID NO: 2 |
| $^{68}$Ga-NODAGA-, | SEQ ID NO: 3 |
| $^{68}$Ga-NOTA-, | SEQ ID NO: 3 |
| $^{68}$Ga-DOTA-, | SEQ ID NO: 3 |
| 68Ga-DOTA-GA-, | SEQ ID NO: 3 |
| $^{18}$F-NODAGA-, | SEQ ID NO: 3 |
| $^{18}$F-NOTA-, | SEQ ID NO: 3 |
| $^{18}$F-DOTA-, | SEQ ID NO: 3 |
| $^{18}$F-DOTA-GA-, | SEQ ID NO: 3 |
| $^{90}$Y-NODAGA-, | SEQ ID NO: 3 |
| $^{90}$Y-NOTA-, | SEQ ID NO: 3 |
| $^{90}$Y-DOTA-, | SEQ ID NO: 3 |
| $^{90}$Y-DOTA-GA-, | SEQ ID NO: 3 |
| $^{111}$In-NODAGA-, | SEQ ID NO: 3 |
| $^{111}$In-NOTA-, | SEQ ID NO: 3 |
| $^{111}$In-DOTA-, | SEQ ID NO: 3 |
| $^{111}$In-DOTA-GA-, | SEQ ID NO: 3 |
| $^{177}$Lu-NODAGA-, | SEQ ID NO: 3 |
| $^{177}$Lu-NOTA-, | SEQ ID NO: 3 |
| $^{177}$Lu-DOTA-, | SEQ ID NO: 3 |
| $^{177}$Lu-DOTA-GA-, | SEQ ID NO: 3 |
| $^{68}$Ga-NODAGA-, | SEQ ID NO: 4 |
| $^{68}$Ga-NOTA-, | SEQ ID NO: 4 |
| $^{68}$Ga-DOTA-, | SEQ ID NO: 4 |
| $^{68}$Ga-DOTA-GA-, | SEQ ID NO: 4 |
| $^{18}$F-NODAGA-, | SEQ ID NO: 4 |
| $^{18}$F-NOTA-, | SEQ ID NO: 4 |
| $^{18}$F-DOTA-, | SEQ ID NO: 4 |
| $^{18}$F-DOTA-GA-, | SEQ ID NO: 4 |
| $^{90}$Y-NODAGA-, | SEQ ID NO: 4 |
| $^{90}$Y-NOTA-, | SEQ ID NO: 4 |
| $^{90}$Y-DOTA-, | SEQ ID NO: 4 |
| $^{90}$Y-DOTA-GA-, | SEQ ID NO: 4 |
| $^{111}$In-NODAGA-, | SEQ ID NO: 4 |
| $^{111}$In-NOTA-, | SEQ ID NO: 4 |
| $^{111}$In-DOTA-, | SEQ ID NO: 4 |
| $^{111}$In-DOTA-GA-, | SEQ ID NO: 4 |
| $^{177}$Lu-NODAGA-, | SEQ ID NO: 4 |
| $^{177}$Lu-NOTA-, | SEQ ID NO: 4 |
| $^{177}$Lu-DOTA-, | SEQ ID NO: 4 |
| $^{177}$Lu-DOTA-GA-, | SEQ ID NO: 4 |
| $^{68}$Ga-NODAGA-, | SEQ ID NO: 5 |
| $^{68}$Ga-NOTA-, | SEQ ID NO: 5 |
| $^{68}$Ga-DOTA-, | SEQ ID NO: 5 |
| $^{68}$Ga-DOTA-GA-, | SEQ ID NO: 5 |
| $^{18}$F-NODAGA-, | SEQ ID NO: 5 |
| $^{18}$F-NOTA-, | SEQ ID NO: 5 |
| $^{18}$F-DOTA-, | SEQ ID NO: 5 |
| $^{18}$F-DOTA-GA-, | SEQ ID NO: 5 |
| $^{90}$Y-NODAGA-, | SEQ ID NO: 5 |
| $^{90}$Y-NOTA-, | SEQ ID NO: 5 |
| $^{90}$Y-DOTA-, | SEQ ID NO: 5 |
| $^{90}$Y-DOTA-GA-, | SEQ ID NO: 5 |
| $^{111}$In-NODAGA-, | SEQ ID NO: 5 |

-continued

| | |
|---|---|
| $^{111}$In-NOTA-, | SEQ ID NO: 5 |
| $^{111}$In-DOTA-, | SEQ ID NO: 5 |
| $^{111}$In-DOTA-GA-, | SEQ ID NO: 5 |
| $^{177}$Lu-NODAGA-, | SEQ ID NO: 5 |
| $^{177}$Lu-NOTA-, | SEQ ID NO: 5 |
| $^{177}$Lu-DOTA-, | SEQ ID NO: 5 |
| $^{177}$Lu-DOTA-GA-, | SEQ ID NO: 5 |
| $^{68}$Ga-NODAGA-, | SEQ ID NO: 6 |
| $^{68}$Ga-NOTA-, | SEQ ID NO: 6 |
| $^{68}$Ga-DOTA-, | SEQ ID NO: 6 |
| $^{68}$Ga-DOTA-GA-, | SEQ ID NO: 6 |
| $^{18}$F-NODAGA-, | SEQ ID NO: 6 |
| $^{18}$F-NOTA-, | SEQ ID NO: 6 |
| $^{18}$F-DOTA-, | SEQ ID NO: 6 |
| $^{18}$F-DOTA-GA-, | SEQ ID NO: 6 |
| $^{90}$Y-NODAGA-, | SEQ ID NO: 6 |
| $^{90}$Y-NOTA-, | SEQ ID NO: 6 |
| $^{90}$Y-DOTA-, | SEQ ID NO: 6 |
| $^{90}$Y-DOTA-GA-, | SEQ ID NO: 6 |
| $^{111}$In-NODAGA-, | SEQ ID NO: 6 |
| $^{111}$In-NOTA-, | SEQ ID NO: 6 |
| $^{111}$In-DOTA-, | SEQ ID NO: 6 |
| $^{111}$In-DOTA-GA-, | SEQ ID NO: 6 |
| $^{177}$Lu-NODAGA-, | SEQ ID NO: 6 |
| $^{177}$Lu-NOTA-, | SEQ ID NO: 6 |
| $^{177}$Lu-DOTA-, | SEQ ID NO: 6 |
| $^{177}$Lu-DOTA-GA- and | SEQ ID NO: 6 |

-continued

| | |
|---|---|
| $^{68}$Ga-NODAGA-S-, | SEQ ID NO: 1 |
| $^{68}$Ga-NOTA-S-, | SEQ ID NO: 1 |
| $^{68}$Ga-DOTA-S-, | SEQ ID NO: 1 |
| $^{68}$Ga-DOTA-GA-S-, | SEQ ID NO: 1 |
| $^{18}$F-NODAGA-S-, | SEQ ID NO: 1 |
| $^{18}$F-NOTA-S-, | SEQ ID NO: 1 |
| $^{18}$F-DOTA-S-, | SEQ ID NO: 1 |
| $^{18}$F-DOTA-GA-S-, | SEQ ID NO: 1 |
| $^{90}$Y-NODAGA-S-, | SEQ ID NO: 1 |
| $^{90}$Y-NOTA-S-, | SEQ ID NO: 1 |
| $^{90}$Y-DOTA-S-, | SEQ ID NO: 1 |
| $^{90}$Y-DOTA-GA-S-, | SEQ ID NO: 1 |
| $^{111}$In-NODAGA-S-, | SEQ ID NO: 1 |
| $^{111}$In-NOTA-S-, | SEQ ID NO: 1 |
| $^{111}$In-DOTA-S-, | SEQ ID NO: 1 |
| $^{111}$In-DOTA-GA-S-, | SEQ ID NO: 1 |
| $^{177}$Lu-NODAGA-S-, | SEQ ID NO: 1 |
| $^{177}$Lu-NOTA-S-, | SEQ ID NO: 1 |
| $^{177}$Lu-DOTA-S-, | SEQ ID NO: 1 |
| $^{177}$Lu-DOTA-GA-S-, | SEQ ID NO: 1 |
| $^{68}$Ga-NODAGA-S-, | SEQ ID NO: 2 |
| $^{68}$Ga-NOTA-S-, | SEQ ID NO: 2 |
| $^{68}$Ga-DOTA-S-, | SEQ ID NO: 2 |
| $^{68}$Ga-DOTA-GA-S-, | SEQ ID NO: 2 |
| $^{18}$F-NODAGA-S-, | SEQ ID NO: 2 |
| $^{18}$F-NOTA-S-, | SEQ ID NO: 2 |
| $^{18}$F-DOTA-S-, | SEQ ID NO: 2 |

-continued

| | |
|---|---|
| $^{18}$F-DOTA-GA-S-, | SEQ ID NO: 2 |
| $^{90}$Y-NODAGA-S-, | SEQ ID NO: 2 |
| $^{90}$Y-NOTA-S-, | SEQ ID NO: 2 |
| $^{90}$Y-DOTA-S-, | SEQ ID NO: 2 |
| $^{90}$Y-DOTA-GA-S-, | SEQ ID NO: 2 |
| $^{111}$In-NODAGA-S-, | SEQ ID NO: 2 |
| $^{111}$In-NOTA-S-, | SEQ ID NO: 2 |
| $^{111}$In-DOTA-S-, | SEQ ID NO: 2 |
| $^{111}$In-DOTA-GA-S-, | SEQ ID NO: 2 |
| $^{177}$Lu-NODAGA-S-, | SEQ ID NO: 2 |
| $^{177}$Lu-NOTA-S-, | SEQ ID NO: 2 |
| $^{177}$Lu-DOTA-S-, | SEQ ID NO: 2 |
| $^{177}$Lu-DOTA-GA-S-, | SEQ ID NO: 2 |
| $^{68}$Ga-NODAGA-S-, | SEQ ID NO: 3 |
| $^{68}$Ga-NOTA-S-, | SEQ ID NO: 3 |
| $^{68}$Ga-DOTA-S-, | SEQ ID NO: 3 |
| $^{68}$Ga-DOTA-GA-S-, | SEQ ID NO: 3 |
| $^{18}$F-NODAGA-S-, | SEQ ID NO: 3 |
| $^{18}$F-NOTA-S-, | SEQ ID NO: 3 |
| $^{18}$F-DOTA-S-, | SEQ ID NO: 3 |
| $^{18}$F-DOTA-GA-S-, | SEQ ID NO: 3 |
| $^{90}$Y-NODAGA-S-, | SEQ ID NO: 3 |
| $^{90}$Y-NOTA-S-, | SEQ ID NO: 3 |
| $^{90}$Y-DOTA-S-, | SEQ ID NO: 3 |
| $^{90}$Y-DOTA-GA-S-, | SEQ ID NO: 3 |
| $^{111}$In-NODAGA-S-, | SEQ ID NO: 3 |
| $^{111}$In-NOTA-S-, | SEQ ID NO: 3 |
| $^{111}$In-DOTA-S-, | SEQ ID NO: 3 |
| $^{111}$In-DOTA-GA-S-, | SEQ ID NO: 3 |
| $^{177}$Lu-NODAGA-S-, | SEQ ID NO: 3 |
| $^{177}$Lu-NOTA-S-, | SEQ ID NO: 3 |
| $^{177}$Lu-DOTA-S-, | SEQ ID NO: 3 |
| $^{177}$Lu-DOTA-GA-S-, | SEQ ID NO: 3 |
| $^{68}$Ga-NODAGA-S-, | SEQ ID NO: 4 |
| $^{68}$Ga-NOTA-S-, | SEQ ID NO: 4 |
| $^{68}$Ga-DOTA-S-, | SEQ ID NO: 4 |
| $^{68}$Ga-DOTA-GA-S-, | SEQ ID NO: 4 |
| $^{18}$F-NODAGA-S-, | SEQ ID NO: 4 |
| $^{18}$F-NOTA-S-, | SEQ ID NO: 4 |
| $^{18}$F-DOTA-S-, | SEQ ID NO: 4 |
| $^{18}$F-DOTA-GA-S-, | SEQ ID NO: 4 |
| $^{90}$Y-NODAGA-S-, | SEQ ID NO: 4 |
| $^{90}$Y-NOTA-S-, | SEQ ID NO: 4 |
| $^{90}$Y-DOTA-S-, | SEQ ID NO: 4 |
| $^{90}$Y-DOTA-GA-S-, | SEQ ID NO: 4 |
| $^{111}$In-NODAGA-S-, | SEQ ID NO: 4 |
| $^{111}$In-NOTA-S-, | SEQ ID NO: 4 |
| $^{111}$In-DOTA-S-, | SEQ ID NO: 4 |
| $^{111}$In-DOTA-GA-S-, | SEQ ID NO: 4 |
| $^{177}$Lu-NODAGA-S-, | SEQ ID NO: 4 |
| $^{177}$Lu-NOTA-S-, | SEQ ID NO: 4 |
| $^{177}$Lu-DOTA-S-, | SEQ ID NO: 4 |
| $^{177}$Lu-DOTA-GA-S-, | SEQ ID NO: 4 |
| $^{68}$Ga-NODAGA-S-, | SEQ ID NO: 5 |

| | |
|---|---|
| $^{68}$Ga-NOTA-S-, | SEQ ID NO: 5 |
| $^{68}$Ga-DOTA-S-, | SEQ ID NO: 5 |
| $^{68}$Ga-DOTA-GA-S-, | SEQ ID NO: 5 |
| $^{18}$F-NODAGA-S-, | SEQ ID NO: 5 |
| $^{18}$F-NOTA-S-, | SEQ ID NO: 5 |
| $^{18}$F-DOTA-S-, | SEQ ID NO: 5 |
| $^{18}$F-DOTA-GA-S-, | SEQ ID NO: 5 |
| $^{90}$Y-NODAGA-S-, | SEQ ID NO: 5 |
| $^{90}$Y-NOTA-S-, | SEQ ID NO: 5 |
| $^{90}$Y-DOTA-S-, | SEQ ID NO: 5 |
| $^{90}$Y-DOTA-GA-S-, | SEQ ID NO: 5 |
| $^{111}$In-NODAGA-S-, | SEQ ID NO: 5 |
| $^{111}$In-NOTA-S-, | SEQ ID NO: 5 |
| $^{111}$In-DOTA-S-, | SEQ ID NO: 5 |
| $^{111}$In-DOTA-GA-S-, | SEQ ID NO: 5 |
| $^{177}$Lu-NODAGA-S-, | SEQ ID NO: 5 |
| $^{177}$Lu-NOTA-S-, | SEQ ID NO: 5 |
| $^{177}$Lu-DOTA-S-, | SEQ ID NO: 5 |
| $^{177}$Lu-DOTA-GA-S-, | SEQ ID NO: 5 |
| $^{68}$Ga-NODAGA-S-, | SEQ ID NO: 6 |
| $^{68}$Ga-NOTA-S-, | SEQ ID NO: 6 |
| $^{68}$Ga-DOTA-S-, | SEQ ID NO: 6 |
| $^{68}$Ga-DOTA-GA-S-, | SEQ ID NO: 6 |
| $^{18}$F-NODAGA-S-, | SEQ ID NO: 6 |
| $^{18}$F-NOTA-S-, | SEQ ID NO: 6 |
| $^{18}$F-DOTA-S-, | SEQ ID NO: 6 |
| $^{18}$F-DOTA-GA-S-, | SEQ ID NO: 6 |
| $^{90}$Y-NODAGA-S-, | SEQ ID NO: 6 |
| $^{90}$Y-NOTA-S-, | SEQ ID NO: 6 |
| $^{90}$Y-DOTA-S-, | SEQ ID NO: 6 |
| $^{90}$Y-DOTA-GA-S-, | SEQ ID NO: 6 |
| $^{111}$In-NODAGA-S-, | SEQ ID NO: 6 |
| $^{111}$In-NOTA-S-, | SEQ ID NO: 6 |
| $^{111}$In-DOTA-S-, | SEQ ID NO: 6 |
| $^{111}$In-DOTA-GA-S-, | SEQ ID NO: 6 |
| $^{177}$Lu-NODAGA-S-, | SEQ ID NO: 6 |
| $^{177}$Lu-NOTA-S-, | SEQ ID NO: 6 |
| $^{177}$Lu-DOTA-S-, | SEQ ID NO: 6 |
| $^{177}$Lu-DOTA-GA-S- | SEQ ID NO: 6 | wherein S is a spacer as defined above.

In a particular embodiment, the conjugated compounds of the invention may be in multimeric form, i.e., comprise several copies of a P or M group, or of both. More specifically, the conjugated compounds may comprise a structure M-P—$X_i$—$P_j$-$M_k$ wherein M and P are as defined above, X is a cross-linking agent, i is an integer selected from 0 or 1, j is an integer selected from 0, 1, 2, 3, 4, or 5, and k is an integer selected from 0, 1, 2, 3, 4, or 5. In such multimeric structures, when i=0, j and k are typically also equal to 0. Furthermore, k may be equal to or below j. Also, in such multimeric structures, M may be linked to P as defined above (i.e., either directly or using a chelator and/or a spacer).

Particular examples of such multimeric compounds have a structure M-P—X—$P_j$-$M_k$ wherein M and P are as defined above, X is a cross-linking agent, j is 1 and k is 0.

The cross-linking agent X may be any chemical cross-linking group compatible for use in the pharmaceutical or veterinary area. The group is preferably devoid of biological activity and toxicity. The size of the cross-linking agent may be adjusted by the skilled person. Preferred examples of X groups are polylysine or polyglutamic platforms (linear, cyclised or branched blocks) or multifunctional organic compounds such as PEG(3)-Pentrimer-G1-(NH2+4×N3)*4HCl with one amino and four azido functions. In a particular embodiment, the cross-linking agent contains at least two reactive functional groups, preferably at least three, allowing coupling of at least 2 peptides. Examples of reactive functional groups include, for instance, amines, acids, thiols, azides, alkynes, carbonyls, or hydrazines. The peptides may be coupled to X either directly, by a covalent bond with a reactive functional group of the agent, or through a spacer, which may be composed for instance of a glycine or a series of glycine, a PEG molecule, or an aminohexanoic acid.

Figure 14:
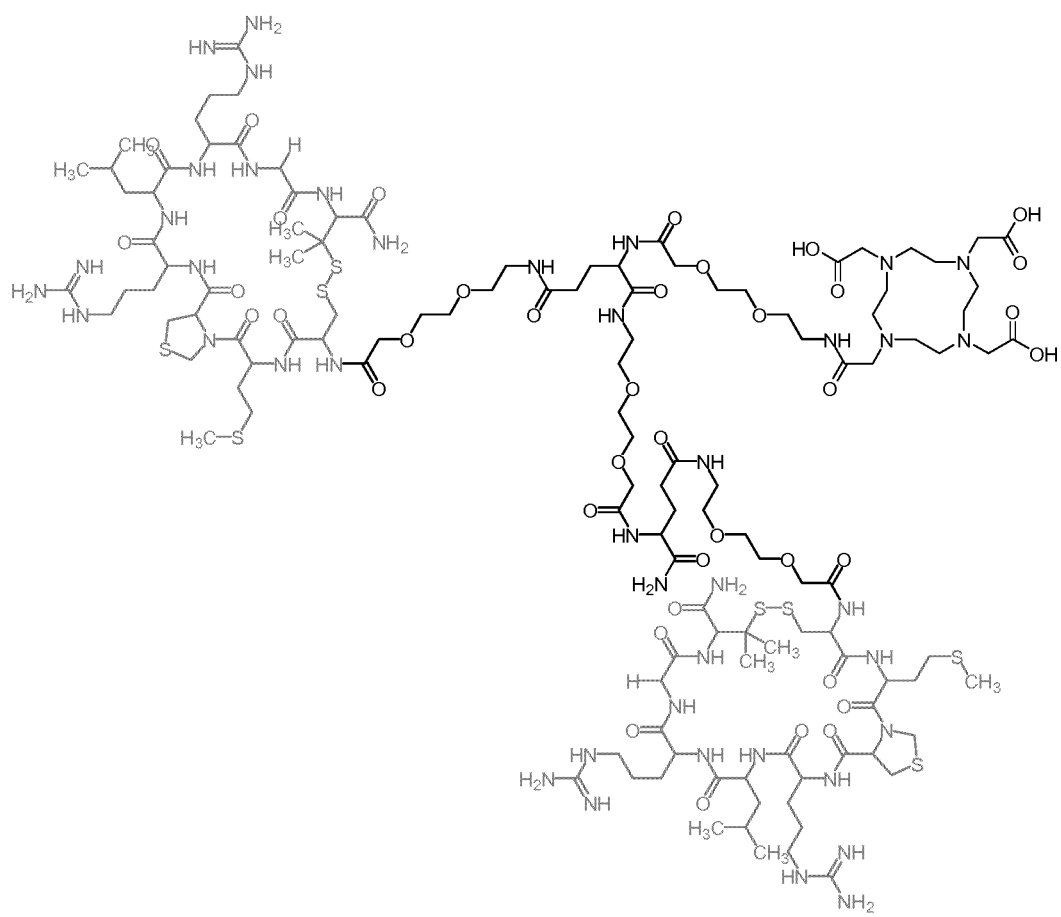
FIG. 14: Structure of compound VHd.

A specific example of such multimeric compound of the invention is compound VHd as represented FIG. 14:

```
DOTA-PEG2-E(PEG2-SEQ ID NO: 1)-PEG2-E
(PEG2-SEQ ID NO: 1)-NH2.
```

The invention also relates to any one of above conjugated compounds devoid of a marker group M. Such compounds are intermediates in the preparation of the final labeled conjugated compounds. Indeed, as shown in the examples, the conjugates are first prepared, and labeling is performed subsequently, typically before administration. The invention thus also relates to any conjugate as defined above which is devoid of M. The invention particularly relates to compounds of structure C—(S—)$_n$P wherein C, S, P and n are defined and coupled as defined above, as well as variants thereof comprising a T group, and/or multimers thereof, as further defined above.

The invention also relates to a pharmaceutical composition comprising at least one conjugated compound as defined above. The composition may comprise one or more pharmaceutically acceptable excipient or diluent.

The invention also relates to a diagnostic composition characterized in that it comprises a diagnostic or medical imaging agent composed of a conjugate compound such as defined above.

Use for Imaging/Diagnosis

The conjugates of the invention can be used to label, detect or diagnose LDLR-expressing cancers in vivo, in any mammal, particularly in human subjects.

In this regard, in a particular embodiment, M is a radionuclide or fluorescent dye adapted for use in imagery, and the labelling and/or detection method comprises:
a) administering the conjugated compound to a subject,
b) performing an imaging method, and
c) analysing the signal obtained in step b),
wherein the presence of a signal is indicative of the presence of cancerous cells and/or of the stage of evolution of a cancer in said subject.

The conjugate may be administered according to various routes. Preferably, the conjugate is injected by systemic, parenteral or local injection. In particular, injection may be intravenous, sub-cutaneous, intramuscular, intraarterial, or intratumoral. In a particular embodiment, the conjugated compound of the invention is injected intravenously. Such a mode of administration allows proper diffusion of the compound in the organism, and reaching of the tissue of interest. In another embodiment, administration is by intratumoral injection. Such a mode is suitable when the presence of a tumor is known or highly suspected, and the method is performed to stage the tumor, assess its progression or the effectiveness of a treatment, for instance.

The amount of compound administered may by adjusted by the skilled person depending on the purpose of the method (imaging, detection, monitoring) and the subject.

The compounds of the invention may be used in various imaging methods known per se in the art, such as, without limitation, scintigraphy, positron emission tomography (PET), positron emission tomography-computed tomography (PET-CT), or single photon emission computed tomography (SPECT). A preferred method is PET.

Depending on the method, the obtained signal may be a quantitative marker value, an image, a distribution curve, a number of positron annihilation events, etc. In step c), such signal is analysed to determine the presence, stage or progression of a cancer in the subject. The term "analysing" refers to any method which allows to determine if a signal corresponds to a normal signal or not. The analyses may not only be visual but also involve quantitative analyses. The analyses may include steps of comparing the value of a signal obtained by imagery to the value of the signal of a known healthy tissue of the same subject or of another subject. The value of the signal may also be compared to a reference value.

A value obtained in step b) more important than a reference value or a control from a healthy tissue is indicative of the presence of cancerous cells. The stage of evolution of a cancer may be assessed by comparing in a same subject a signal obtained after two different imaging sessions spaced in time.

The conjugated compounds of the invention are particularly adapted for labelling and/or detecting cancerous cells that overexpress LDLR. In this regard, the term "cells that overexpress LDLR" refers to cells that express at least 10% more LDLR with respect to a standard level of expression. Typically, 1000 to 3000 LDLR are present at the surface of "normal" cells. LDLR-overexpressing cells are cells that express at least 20% more LDLR, more particularly at least 50%, 75%, 100%, or 150% more LDLR.

Specific examples of LDLR-overexpressing cancers that can be detected using the present method include pancreatic cancer, adrenal cancer, glioblastoma, prostate cancer, colon cancer, liver cancer, pancreas cancer, ovaries cancer, lung cancer or stomach cancer.

Radiotherapy

In a further aspect, the invention also relates to the use of the conjugated compounds of the invention to treat cancer by radiotherapy.

The terms "treatment," "treating," "treat" and other similar expressions refer to obtaining a pharmacological and/or physiological effect, for example, inhibition of cancer cell growth or improving cancer cell death.

In this regard, the treatment method comprises administering to a subject in need thereof a conjugated compound as defined above.

Preferably, the conjugated compound comprises a radionuclide suitable for radiotherapy, such as beta- or high energy gamma-emitting radionuclides, preferably with a long half-life (e.g., between 1 to 75 days). Preferred radionuclides for use in radiotherapy are selected from $^{90}$Y, $^{111}$In, $^{131}$I, and $^{177}$Lu. In a preferred embodiment, $^{90}$Y, $^{177}$Lu or $^{111}$In are used.

The conjugate may be administered according to various routes. Preferably, the conjugate is injected by systemic, parenteral or local injection. In particular, injection may be intravenous, sub-cutaneous, intramuscular, intraarterial, or intratumoral. In a particular embodiment, the conjugated compound of the invention is injected intravenously. Such a mode of administration allows proper diffusion of the compound in the organism, and reaching of the tissue of interest. In another embodiment, administration is by intratumoral injection.

The compound should be administered in an amount sufficient to irradiate the tumor. Such amount may be adjusted by the skilled artisan.

The treatment may be used either alone, or in combination with (e.g., in alternance or conjunction with) other cancer therapies such as chemotherapy for instance.

The method may be used to treat any LDLR-overexpressing cancer, such as pancreatic cancer, adrenal cancer, glioblastoma, prostate cancer, colon cancer, liver cancer, pancreas cancer, ovaries cancer, lung cancer or stomach cancer. It may be used at any stage of development of the cancer, in any mammalian subject, particularly human subjects. Typically, several sequential treatment regimens are performed. For use in therapy, the conjugate compounds of the invention can be in the form of any pharmaceutically acceptable salts. The expression "pharmaceutically acceptable salts" refers to, for example and in a non-restrictive way, pharmaceutically acceptable base or acid addition salts, hydrates, esters, solvates, precursors, metabolites or stereoisomers. The expression "pharmaceutically acceptable salts" refers to nontoxic salts, which can be generally prepared by reacting a free base with a suitable organic or inorganic acid. These salts preserve the biological effectiveness and the properties of free bases. Representative examples of such salts include water-soluble and water-insoluble salts such as acetates, N-methylglucamine ammonium, amsonates (4,4-diaminostilbene-2,2'-disulphonates), benzenesulphonates, benzonates, bicarbonates, bisulphates, bitartrates, borates, hydrobromides, bromides, buryrates, camsylates, carbonates, hydrochlorates, chlorides, citrates, clavulanates, dichlorhydrates, diphosphates, edetates, calcium edetates, edisylates, estolates, esylates, fumarates, gluceptates, gluconates, glutamates, glycolylarsanylates, hexafluorophosphates, hexylresorcinates, hydrabamines, hydroxynaphthoates, iodides, isothionates, lactates, lactobionates, laurates, malates, maleates, mandelates, mesylates, methylbromides, methylnitrates, methylsulphates, mucates, napsylates, nitrates, 3-hydroxy-2-naphthoates, oleates, oxalates, palmitates, pamoates (1,1-methylene-bis-2-hydroxy-3-naphtoates, or emboates), pantothenates, phosphates, picrates, polygalacturonates, propionates, p-toluenesulphonates, salicylates, stearates, subacetates, succinates, sulphates, sulphosalicylates, suramates, tannates, tartrates, teoclates, tosylates, triethiodides, trifluoroacetates and valerianates.

Also, the conjugate compounds may be formulated with any suitable pharmaceutical excipient, carrier or diluent. In this regard, the invention also relates to compositions comprising a compound as defined above and a pharmaceutically acceptable carrier or excipient. The pharmaceutically acceptable carrier can be selected from the carriers classically used according to each mode of administration. According to the mode of administration envisaged, the compounds can be in solid, semi-solid or liquid form. For solid compositions such as tablets, pills, powders, or granules that are free or are included in gelatin capsules, the active substance can be combined with: a) diluents, for example lactose, dextrose, sucrose, mannitol, sorbitol, cellulose and/or glycine; b) lubricants, for example silica, talc, stearic acid, its magnesium or calcium salt and/or polyethylene glycol; c) binders, for example magnesium and aluminum silicate, starch paste, gelatin, tragacanth, methylcellulose, sodium carboxymethyl cellulose and/or polyvinylpyrrolidone; d) disintegrants, for example starch, agar, alginic acid or its sodium salt, or effervescent mixtures; and/or d) absorbents, dyes, flavoring agents and sweeteners. The excipients can be, for example, mannitol, lactose, starch, magnesium stearate, sodium saccharin, talc, cellulose, glucose, sucrose, magnesium carbonate and analogues of pharmaceutical quality. For semi-solid compositions such as suppositories, the excipient can, for example, be an emulsion or oily suspension, or polyalkylene glycol-based, such as polypropylene glycol. Liquid compositions, in particular injectables or those included in a soft capsule, can be prepared, for example, by dissolution, dispersion, etc., of the active substance in a pharmaceutically pure solvent such as, for example, water, physiological saline solution, aqueous dextrose, glycerol, ethanol, oil and analogues thereof.

The compositions or conjugates of the invention can be administered by any suitable route and, in a non-restrictive way, by parenteral route, such as, for example, in the form of preparations that can be injected by intravenous, infusion, subcutaneous or intramuscular route; by oral route (or per os), such as, for example, in the form of coated or uncoated tablets, gelatin capsules, powders, pellets, suspensions or oral solutions (one such form for oral administration can be either with immediate release or with extended or delayed release); by rectal route such as, for example, in the form of suppositories; by topical route, in particular by transdermal route, such as, for example, in the form of patches, pomades or gels; by intranasal route such as, for example, in aerosol and spray form; by perlingual route; or by intraocular route.

The invention also relates to a method for preparing or making a conjugate compound as defined above, comprising coupling a marker M to a peptide P, preferably using a chelator agent C.

The invention also relates to a method for making a pharmaceutical composition, comprising providing a conjugate compound as defined above and formulating said compound with a suitable excipient or diluent.

Other aspects and advantages of the present invention will become apparent upon consideration of the examples below, which are only illustrative in nature and which do not limit the scope of the present application.

EXAMPLES

Example 1: LDL-Receptor (LDLR) Expression in Mouse and Human Tissues

In order to assess membrane expression of LDLR in mouse and human cell lines of interest, the kit ProteoExtract Subcellular Proteome Extraction Kit (Calbiochem, La Jolla, Calif., USA) was used to prepare membrane extracts from human and mouse cancerous cell lines.

Membrane extracts were quantified using the BioRad DC Protein Assay (Bio-Rad, Hercules, Calif., USA) following manufacturer's instructions. One, 10 µg or 20 µg of membrane cell proteins were separated by sodium dodecyl sulfate polyacrylamide gel electrophoresis (SDS-PAGE) on 4-12% polyacrylamide gels, and transferred onto nitrocellulose membranes (Amersham Biosciences). Membranes were probed with a goat anti-LDLR antibody (R&D Systems, (1/500)), followed by a peroxidase conjugated donkey anti-goat secondary antibody (Jackson Immunoresearch). Finally, proteins were detected using chemiluminescence.

As shown in FIG. 1 A, LDLR expression is enhanced in adrenal (NCI-H295R), glioblastoma (U87MG), breast cancer (MDA-MB-231) and in prostate (PC3) human cancerous cells. CHO95 (Engineered Chinese Hamster Ovary cells stably expressing hLDLR fused to GFP (hLDLR-GFP) is used as a positive control. In human pancreatic cancerous cells (Capan, BxPC3 and Panc1) the level of LDLR is variable. In other cell types, like Hela (Cervix cancer) or MCF7 breast cancer cells, the expression levels of LDLR are very low, almost undetectable. LDLR expression is enhanced in a mouse pancreatic cell line PK4A (derived from a mouse that develops spontaneous tumors in the pancreas) compared to normal pancreatic tissue.

Example 2: Synthesis of Fluorescent LDLR Targeting Conjugates: Conjugate A, Conjugate B, Conjugate C and Conjugate D In the following examples, the production and uses of conjugates A, B, C, and D are disclosed. Conjugates A, B, C, and D contain, respectively, peptides A (SEQ ID NO: 1), B (SEQ ID NO: 13), C (SEQ ID NO: 6), and D (SEQ ID NO: 14), as shown below.

| Compound | Composition |
|---|---|
| Conjugate A | Fc-Peptide A-A680 |
| Conjugate B | Fc-Peptide B-A680 |
| Conjugate C | Fc-Peptide C-A680 |
| Conjugate D | Fc-Peptide D-A680 |

Conjugate C and Conjugate D Fusion Protein Production

Peptides C and D were cloned in fusion with the Fc fragment of an IgG1.

In order to produce the Fc fragment fused to peptide C or D, a plasmid construct was generated based on the plasmid pINFUSE hIgG1-Fc2 (InvivoGen) that was used as template. Mega-primers called primer C or primer D were synthesized by PCR using the oligonucleotides:

```
Forward primer:
                                            (SEQ ID NO: 10)
CTTGGCATTATGCACCTCCA Reverse primer containing the sequence coding for
the peptide C:
                                            (SEQ ID NO: 11)
CTGGCCAGCTAGCACTCAGCAACCGCGAAGACGAGGCATACAAGCACCT
TTACCCGGAGACAGGGAG.

Reverse primer containing the sequence coding for
the peptide D:
                                            (SEQ ID NO: 12)
CTGGCCAGCTAGCACTCGCAGGGTCTGCCCAGCATTCTGCAAGCACCTT
TACCCGGAGACAGGGAG.
```

The product of the PCR reaction was purified, digested with DpnI (enzyme that digests the parental methylated DNA) and used as a mega primer in a second PCR reaction performed with the pINFUSE hIgG1-Fc2 plasmid used as matrix using the QuickChange II Site Directed Mutagenesis Kit (Agilent). After transformation of competent bacteria, isolated colonies were obtained, plasmid DNA was prepared and the cDNA construct was sequenced on both strands for verification. The vectors called pConjugate-C and pConjugate-D allow expression of the Fc fragment fused in C-terminus with peptides C and D after transfection of mammalian cells. Expi293 expression system (Thermo Fischer) was used for the transient expression of fusion protein conjugates C and D in culture supernatants. After 72 hours of transfection, supernatants were recovered and purified using the Montage antibody protein A PROSEP A kit (Millipore) according to the manufacturer's recommendations.

Conjugate A and Conjugate B Protein Synthesis:

Conjugation of peptides A and B to the human IgG1 Fc fragment (Merck Millipore) was performed using the heterobifunctional spacer sulfo-SMCC (Pierce Biotechnology, Rockford, Ill., USA) in a two-step fashion. First, the Fc fragment was allowed to react with sulfo-SMCC to obtain a reactive protein against thiol moieties; in a second step thiol-functionalized peptides A or B were conjugated to the lysine-linked Fc-SMCC protein.

Thiol-Functionalized Peptides Synthesis

Peptide A and peptide B amino acid sequences are respectively cMThzRLRGPen (SEQ ID NO: 1) and cRPLGRMC (SEQ ID NO: 13) where "Thz" refers to thiazolidine and "Pen" to penicillamine.

N-α-Fmoc-protected amino acids were chosen with standard orthogonal side chain protections: Fmoc-Cys(Trt)-OH (in configuration D or L), Fmoc-Pen(Trt)-OH, Fmoc-Met-OH, Fmoc-Pro-OH, Fmoc-Thz-OH, Fmoc-Arg(Pbf)-OH, Fmoc-Leu-OH, and Fmoc-Gly-OH. They were all purchased from Iris Biotech as well as Piperidin, Trifluoroacetic acid (TFA), Diisopropylethylamine (DIEA), ethanedithiol (EDT), Triisopropylsilane (TIS), benzotriazol-1-yl-oxytripyrrolidinophosphonium hexafluorophosphate (Py-Bop), 1-[Bis(dimethylamino)methylene]-1H-1,2,3-triazolo[4,5-β]pyridinium 3-oxid hexafluorophosphate (HATU) and 2-Tritylthio-1-ethylamine hydrochloride (Trt-cysteamine).

Dimethylformamide (DMF), propionic anhydride, AcOH, K3 [Fe(CN)6], ammonium carbonate and dichloromethane (DCM) were purchased from Sigma-Aldrich.

Both Pr-Peptide A-G-$CH_2$—$CH_2$—SH and Pr-Peptide B-G-$CH_2$—$CH_2$—SH were synthesized by solid phase peptide synthesis (SPPS) method using a Fmoc/tBu strategy and a Fmoc-Gly-Wang Resin (100-200 mesh, 1% DVB, loading 0.7 mmol/g) purchased from Iris Biotech. Such a resin allows synthesis of peptides completely deprotected on their side chains and having a free carboxylic acid at their C-termini. A Gly residue was inserted at the C-ter position to enable functionalization while avoiding racemization.

Peptide synthesis was performed on a Liberty™ (CEM) microwave synthesizer for cMThzRLRGPen and cRPL-GRMC sequences.

For automated synthesis, amino acids were coupled via micro-wave activation of the acid function of the n+1 amino acid using aa/DIEA/HATU: 4/4/8 equivalent (with respect to the resin) in a 0.25 mmol scale synthesis. Coupling time was adjusted to 10 min. Double couplings were necessary for amino acids introduced after Thiazolidine or Proline residues. Deprotection of the Fmoc group of a new amino acid thus coupled was carried out using 20% piperidin in DMF. The last amino acid coupled during peptide elongation was deprotected and N-propionylated using propionic anhydride (2*5 min $Pr_2O$/DCM: 1/1).

Resin-bound peptides were then cleaved using a solution comprised of TFA/TIS/H2O/EDT: 94/2/2/2 for at least 2 hours at room temperature (RT). A minimum of 15 mL of cleavage solution were used per gram of resin. Crude peptides were then precipitated using ice-cold ether, centrifuged at 3000 rpm for 8 min and lyophilized in $H_2O$/0.1% TFA. White solids were obtained and engaged in the cyclisation step without any further purification.

Disulfide bridges were obtained by intramolecular cyclization from two thiol functions of two suitably protected Cys or Pen, either in configuration L or D. Crude Pr-cMThzRLRGPen-G-OH and Pr-cRPLGRMC-G-OH were dissolved in AcOH 0.5% to obtain a 0.5 mg/mL final concentration. Ammonium carbonate (2N) was added to the peptide solutions to reach an approximate basic pH of 8-9. $K_3[Fe(CN)_6]$ (0.01N) was then added to the reaction mixtures until a bright and persistent yellow color was observed. Monitoring of the reactions was performed by analytical RP-HPLC. Usually reactions were quantitative in less than 30 min. Reaction mixtures were filtered on a 0.45 µm membrane and purified by preparative RP-HPLC. Fractions with purities above 95% were collected and lyophilized to give pure white powders (final purity>95%). The homogeneity and identity of the pure synthetic peptides were assessed by analytical RP-HPLC. Peptides were satisfactorily checked for identity by ESI mass spectrometry on LCQ Fleet (ThermoFisher) used in positive mode.

Thiol functionalization of Pr-Peptide B-G-OH and Pr-Peptide A-G-OH was performed on their C-termini using cysteamine via: i) activation of the first Gly residue with PyBop/DIEA in DMF and reaction with 2-tritylthio-1-ethylamine hydrochloride (Trt-cysteamine) and ii) removal of cysteamine trityl protections in acidic conditions (DCM/TIS/TFA: 3/1/1).

Chemical Conjugation of Pr-Peptide A-G-CH$_2$—CH$_2$—SH and Pr-Peptide B-G-CH$_2$—CH$_2$—SH to Fc Fragment In a first step, peptides A and B were functionalized with a sulfo-SMCC spacer: Peptide A-SMCC and Peptide B-SMCC, were allowed to react with the primary amines of a human Fc fragment (AG 714-Millipore) using a molar excess of 25 peptides per Fc. The reaction incubated at room temperature (RT) for 1 hour in PBS buffer. To remove excess peptides the mixture was then purified on a Pierce™ Dextran Desalting Columns (Pierce). Fc-Peptide A and Fc-Peptide B conjugates concentrations were determined using an anti-Fc ELISA assay.

Chemical Synthesis of Conjugates A, B, C and D

To conjugate the fluorophore Alexa680™ (A680 excitation: 679 nm; emission: 702 nm) to Fc-Peptide A, Fc-Peptide B, Fc-Peptide C and Fc-Peptide D, the SAIVI™ Rapid Antibody Labeling kit (S30045-ThermoFicher) was used. This kit is designed to label antibodies with an optimal degree of labeling (DOL, dye-to-protein ratio) for in vivo imaging applications (DOL, of about 2). The DOL of each conjugate (see table I) can be determined by absorption spectroscopy making use of the Lambert-Beer law: Absorbance (A)=extinction coefficient ($\varepsilon$)×molar concentration× path length (d). The UV-VIS spectrum of the conjugate solution is measured. Determination of the absorbance (Amax) at the absorbance maximum ($\lambda$abs) of the dye and the absorbance (A280) at 280 nm (absorption maximum of proteins) give access to the concentration of bound dye given by c(dye)=Amax/$\varepsilon$max×d, where $\varepsilon$max is the extinction coefficient of the dye at the absorption maximum and to the protein concentration in the same way from its absorbance at 280 nm: c(protein)=Aprot/$\varepsilon$prot×d, where $\varepsilon$prot is the extinction coefficient of the protein at 280 nm. DOL is then calculated as follows: DOL=[Amax/$\varepsilon$max]/[Aprot/$\varepsilon$prot].

TABLE I

DOL of conjugates

| Conjugate name | DOL |
| --- | --- |
| Conjugate A | 1.3 |
| Conjugate B | 1.5 |
| Conjugate C | 1.3 |
| Conjugate D | 1.8 |

Conjugates A, B, C and D concentrations were determined using an anti-Fc ELISA assay.

Example 3: Surface Plasmon Resonance (SPR) Determination of Conjugate A, B, C and D Affinity ($K_D$) for LDLR. Binding/Endocytosis Properties of Conjugates to h/m LDLR Stably Expressed by CHO Cells and Cancerous Cell Lines Affinity ($K_D$) of Conjugates for LDLR Recombinant human LDLR (His-tagged) was purchased from Sino Biological (Beijing, China). Interaction of conjugates with LDLR was tested at 25° C. using a Biacore T200 (GE Healthcare) and 50 mM HEPES-NaOH pH7.4, 150 mM NaCl, 0.005% Tween-20, 50 µM EDTA as running buffer. hLDLR was immobilized on a NiHC sensor chip (Xantec, Dusseldorf, Germany) at a density of 35-60 fmol/mm$^2$. Binding of conjugates to LDLR-coated flow cells was corrected for non-specific binding to uncoated flow cells. The single-cycle kinetic method was used to measure the affinity of ligands with LDLR. Ligands were diluted in running buffer and injected sequentially 2 minutes at 30 µl/min using increasing concentrations. Blank run injections of running buffer were performed in the same conditions before ligand injection. Double-subtracted sensorgrams were globally fitted with the 1:1 Langmuir binding model from Biacore T200 Evaluation version 2.0. $K_{Ds}$ are summarized in the following table II:

TABLE II

Affinity of conjugates A, B, C and D for human LDLR.

| Conjugate name/ID | kon (M$^{-1}$s$^{-1}$) | koff (s$^{-1}$) | $K_D$ (pM) |
| --- | --- | --- | --- |
| Conjugate A | 1.20E+06 | 1.38E−04 | 115 |
| Conjugate B | | No Binding | |
| Conjugate C | 2.89E+05 | 2.44E−04 | 835 |
| Conjugate D | | No Binding | |

Binding/Endocytosis of Fluorescent Conjugates by LDLR Expressing Cells

To evaluate the ability of conjugates with affinity for h/mLDLR-GFP (conjugates A and C) and control conjugates (conjugates B and D) to be endocytosed by the LDLR, immunocytochemical experiments involving the incubation of all the conjugates on live hLDLR-GFP cells were performed during 1 hour at 37° C. followed by confocal microscopy analysis.

In these experiments, with regards to FIG. 2, the LDLR-GFP signal is visualized in column 2, the conjugate signal is either directly visualized in column 4 using the A680 fluorescence or in column 3 using an anti-hFc-A594 conjugated secondary antibody. Cell nuclei were stained in blue with Hoechst and its signal can be visualized in column 1. The co-labelling of LDLR-GFP and conjugates can be visualized as a highlight signal in column 5 on the merge image. The results obtained indicate that the conjugates A and C bind to and are endocytosed by CHO-hLDLR-GFP cells whereas control conjugates B or D are not.

Example 4: ELISA Quantification of the Distribution of LDLR Targeting Conjugates i.v Injected in Naïve or Cancer Bearing Mice Mouse pancreatic adenocarcinoma PK4A cells were obtained from S. Vasseur (Inserm U1068, Cellular Stress) and previously described (Guillaumond F et al. 2013 Proc Natl Acad Sci USA 110(10):3919-3924). Cells were cultured in Dulbecco's modified Eagle's medium (DMEM; Invitrogen, Carlsbad, Calif.) supplemented with penicillin (100 U/mL), streptomycin (100 µg/mL), fetal bovine serum (10% Gold Serum, InVitrogen) and incubated at 37° C. in an atmosphere containing 5% CO$_2$. Cells were used for tumor induction. PK4A tumor xenografts were induced in 4 week's old Hsd: Athymic Nude-Foxn1nu Nude Mouse male obtained from Envigo (Harlan, Indianapolis, Ind.) by subcutaneous injection between the shoulders of 1×10$^6$ cells suspended in 150 µL of complete medium. Tumor size was visually assessed every other day and the animals were used for in vivo imaging experiments. Once the PK4A subcutaneous tumor volume had reached approximately 700-1500 mm$^3$ in size (10 to 14 days post implantation), tumor-bearing mice were injected in the tail vein with 5 nmoles of conjugates. After 2 hours for the conjugates A and B, and 4 hours for the conjugates C and D, whole blood was collected in heparinized tubes (Sigma Aldrich) and plasma was isolated after 15 min centrifugation at 5000 g. Mice were then perfused with PBS 1× at a rate of 2 ml/min for 10 min. Organs were extracted, weighed, and homogenized in PBS/ 0.1% Triton (Sigma Aldrich) in PBS containing a protease inhibitor cocktail (Sigma Aldrich). Organ homogenates were frozen at −80° C. for 12 hrs before sonication 3×10 s and clarification of the tissue lysates was performed by centrifugation for 15 min at 20000 g. Fc concentrations in the isolated supernatants were measured with an anti-Fc ELISA. Results in FIG. 3 show a 40-fold accumulation of conjugate A and 30-fold accumulation of conjugate C in pancreatic tumor vs pancreas. Kidney accumulation is shown as control.

Figure 4:
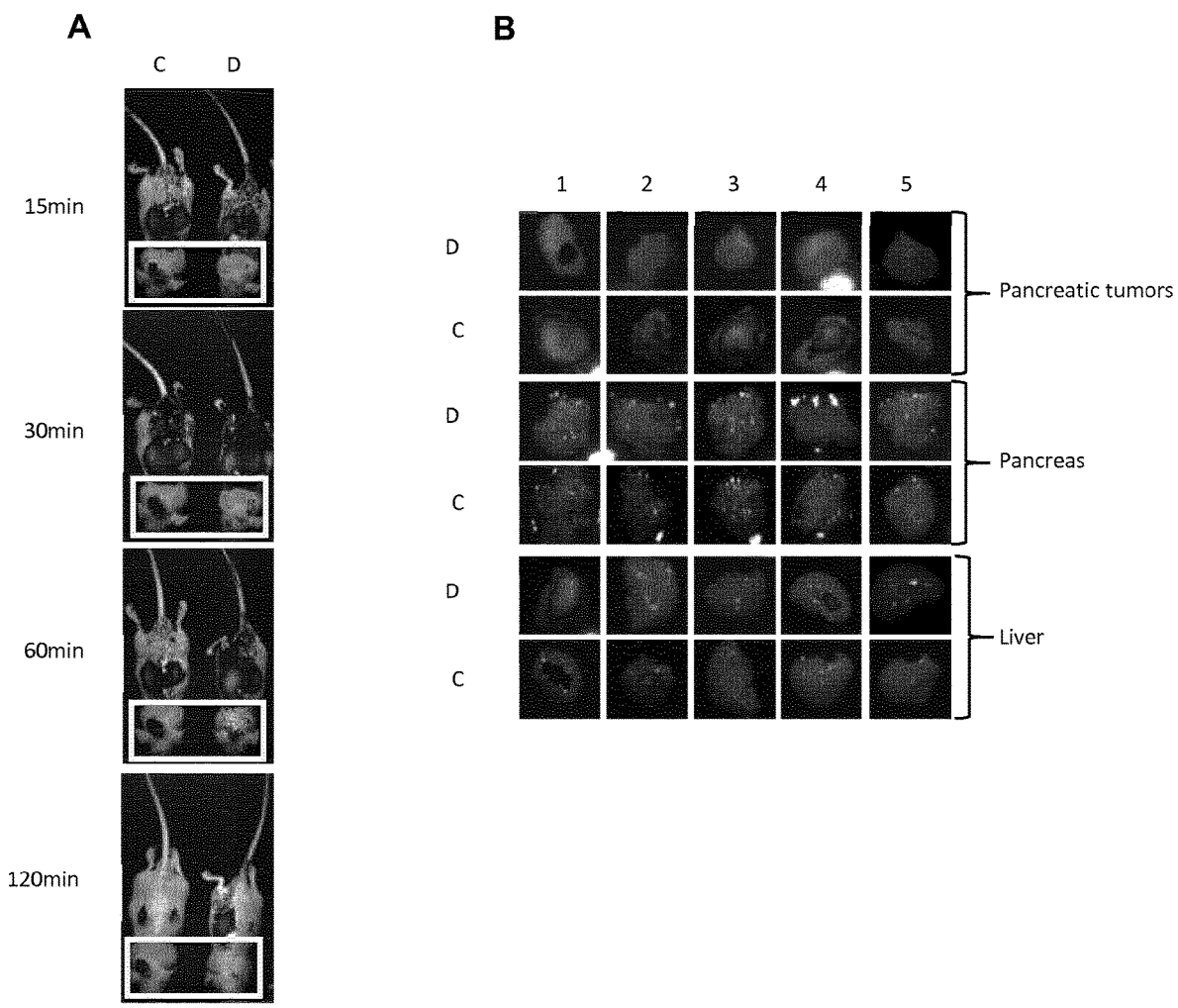
FIG. 4: In A, whole-body fluorescence imaging of mice implanted with PK4A tumour and analysed 15 min, 30 min, 60 min and 120 min after intravenous injection of conjugate C or conjugate D (control). In B, ex-vivo imaging of pancreatic tumour, healthy pancreas and liver harvested 4 h after intravenous injection of conjugate C or conjugate D (control).

Example 5: Biodistribution of Conjugate C and its Scrambled Counterpart Conjugate D in Pancreatic Tumor and Healthy Pancreas Tumor-bearing mice were injected intravenously with 5 nmol of conjugate C, along with conjugate D as a control (n=5). Fluorescence whole-body imaging was monitored at 15 min, 30 min, 60 min and 120 min after IV injection. The pancreas, liver, and tumor tissues were harvested at the end of the experiment (4 h after IV injection of the molecules), and fluorescence ex-vivo was measured. FIG. 4 shows that conjugate C accumulates significantly in the pancreatic tumour, compare to the scrambled conjugate D. Furthermore, this accumulation was specific for the pancreatic tumor since no accumulation was observed in the healthy pancreatic tissue.

Example 6: Synthesis of NODAGA-SEQ ID NO: 1-NH$_2$, DOTA-SEQ ID NO: 1-NH$_2$, NODAGA-βAla-PEG12-SEQ ID NO: 1-NH$_2$, DOTA-βAla-PEG12-SEQ ID NO: 1-NH$_2$ and their Respective Scramble Control NODAGA-βAla-PEG12-SEQ ID NO: 13-NH$_2$ and DOTA-βAla-PEG12-SEQ ID NO: 14-NH$_2$ In the following examples, $^{68}$Ga-CH44 is used as an abbreviation for $^{68}$Ga-NODAGA-βAla-PEG12-SEQ ID NO: 1-NH$_2$, $^{68}$Ga-FG770 is used as an abbreviation for $^{68}$Ga-DOTA-βAla-PEG12-SEQ ID NO: 1-NH$_2$, $^{68}$Ga-CH40 is used as an abbreviation for $^{68}$Ga-NODAGA-βAla-PEG12-SEQ ID NO: 13-NH$_2$, and $^{68}$Ga-FG769 is used as an abbreviation for $^{68}$Ga-DOTA-βAla-PEG12-SEQ ID NO: 13-NH$_2$.

| Abbreviation | Compound |
|---|---|
| $^{68}$Ga-CH44 | $^{68}$Ga-NODAGA-βAla-PEG12-SEQ ID NO: 1-NH$_2$ |
| $^{68}$Ga-CH40 | $^{68}$Ga-NODAGA-βAla-PEG12-SEQ ID NO: 13-NH$_2$ |
| $^{68}$Ga-FG770 | $^{68}$Ga-DOTA-βAla-PEG12-SEQ ID NO: 1-NH$_2$ |
| $^8$Ga-FG769 | $^{68}$Ga-DOTA-βAla-PEG12-SEQ ID NO: 13-NH$_2$ |

Two types of chelating cages were conjugated to LDLR-targeting peptide vectors:

NODAGA (1,4,7-triazacyclononane-1-glutaric acid-4,7-diacetic acid) enables the synthesis of radio labeled conjugates for imaging;

DOTA (tetraazacyclododecane-1,4,7,10-tetraacetic acid) has been introduced for the preparation of radio labeled conjugates for with a potential for radiotherapy.

The macrocyclic NOTA (1,4,7-triazacyclononane-1,4,7-triacetic acid) and NODAGA are the most favorable ligands for the chelation of $^{68}$Gallium which is a commonly used radiotracer. Among these ligands NODAGA has been chosen as this chelating cage contains an additional coupling moiety compared to NOTA. This ensures that all of the carboxylic arms are available to saturate the hexadentate coordination.

For radiotherapy $^{111}$Indium, $^{177}$Lu or $^{90}$Yttrium are clinically used. Such radiometals fit well in DOTA macrocyclic chelators with which they form thermodynamically and kinetically stable complexes. Indeed, DOTA provides eight donor atoms and the appropriate cavity size to form more stable complexes with these radionuclides.

Both NODAGA and DOTA derivatives were prepared to develop imaging agents and receptor-mediated radiotherapy able to preferentially target LDLR-expressing cancers.

Different constructs were designed and prepared to assess the position and the distance of the macrocyclic chelator conjugated to the peptide vectors: the chelating agent was either conjugated to the C-terminus, the N-terminus or to the amino-side chain of a lysine additionally introduced to the peptide vector sequence. All derivatives always bound to the target LDL-receptor as assessed by SPR analysis on purified LDLR. We thus chose the construct bearing the chelating agent at the N-terminus as this synthesis route is easier to set up.

Figure 5:
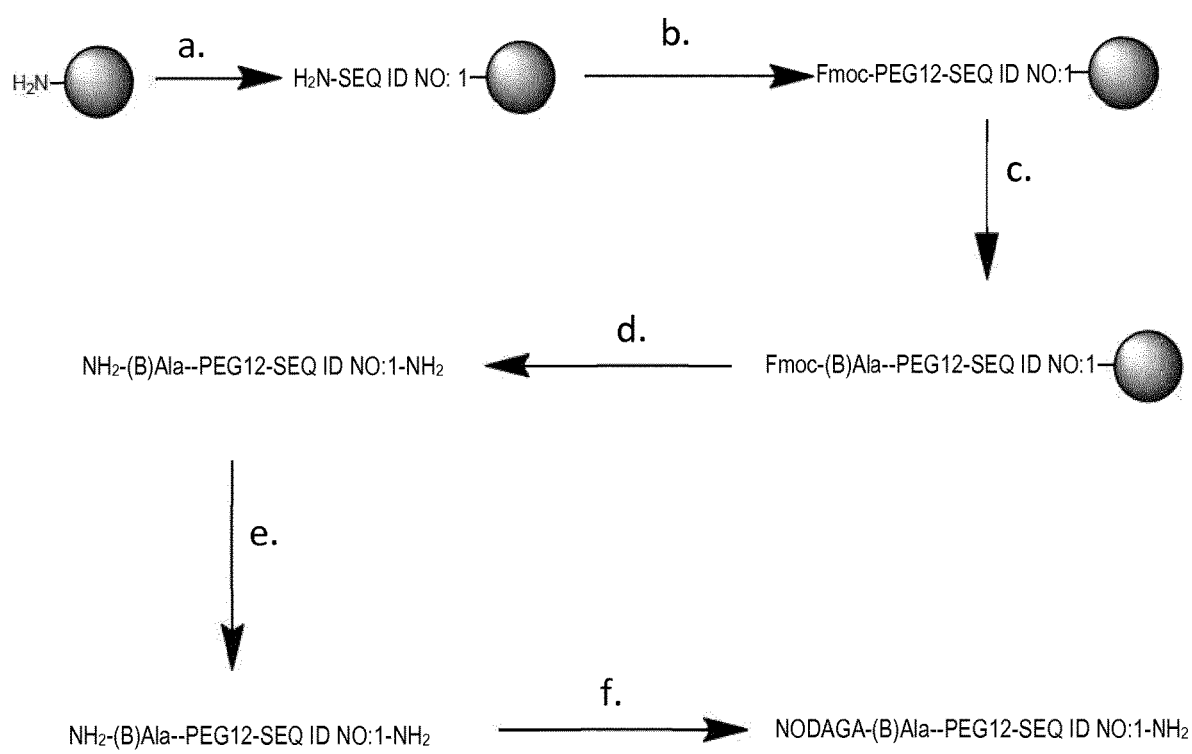
FIG. 5: Reaction scheme for the synthesis of cage-βAla-PEG12-Peptide-NH$_2$ compounds. In the present scheme, the synthesis of NODAGA-βAla-PEG12-SEQ ID NO: 1-NH$_2$ is shown as an example.

FIG. 5 represents the reaction scheme for the synthesis of cage-linker-peptide-NH$_2$ conjugates. In the present scheme, the example of the synthesis of NODAGA-βAla-PEG12-SEQ ID NO: 1-NH$_2$ is shown.

The reagents and conditions of the synthesis reaction are as follows with reference to FIG. 5:

step a: AA (4 equivalent (eq)), HATU (4 eq), DIEA (8 eq), DMF, micro-wave activation;

step b: Fmoc-PEG12-OH (1.5 eq), DIC (4 eq), HOBt (2 eq), DMF, Room Temperature (RT), 24 h;

step c: Fmoc-(β)Ala-OH (3 eq), COMU (3 eq), DIEA (8 eq), DMF, RT, 3 h;

step d: DMF/piperidin (20%) 15 min, TFA/TIS/H$_2$O/EDT (94/2/2/2), RT, 2 h;

step e: AcOH (0.5%), (NH$_4$)$_2$CO$_3$, K$_3$Fe(CN)$_6$, pH=7-8, [peptide]=1 mg/mL;

step f: NODAGA-NHS (2 eq), DIEA (10 eq), DMF, RT, 30 min.

Analytical and Purification Methods:

Reaction progress and purity monitoring were carried out on a Thermo Fisher UltiMate® 3000 system equipped with a C18 Kinetex™ (5 μm, 150 mm×4.6 mm). Detection was done at 214 nm. Elution system was composed of H2O/0.1% TFA (solution A) and MeCN/0.1% TFA (solution B). Flow rate was 2 mL/min with a gradient of 0-100% of solution B in 4 min.

Crude products were purified by RP-HPLC on a Thermo Fisher UltiMate® 3000 system equipped with a C18 Luna™ (5 μm, 100 mm×21.2 mm). Detection was done at 214 nm. Elution system was composed of H2O/0.1% TFA (solution A) and MeCN/0.1% TFA (solution B). Flow rate was 20 mL/min.

Synthesis of H-SEQ ID NO: 1-NH$_2$, H-βAla-PEG12-SEQ ID NO: 1-NH$_2$ and H-βAla-PEG12-SEQ ID NO: 13-NH$_2$:

N-α-Fmoc-protected amino acids were chosen with standard orthogonal side chain protections: Fmoc-Cys(Trt)-OH (in configuration D or L), Fmoc-Pen(Trt)-OH, Fmoc-Met-OH, Fmoc-Pro-OH, Fmoc-Thz-OH, Fmoc-Arg(Pbf)-OH, Fmoc-Leu-OH, Fmoc-βALa-OH, and Fmoc-Gly-OH. They were all purchased from Iris Biotech as well as Piperidin, Trifluoroacetic acid (TFA), Diisopropylethylamine (DIEA), ethanedithiol (EDT), Triisopropylsilane (TIS), 1-Cyano-2-ethoxy-2-oxoethylidenaminooxy)dimethylamino-morpholino-carbenium hexafluorophosphate (COMU), 1-[Bis (dimethylamino)methylene]-1H-1,2,3-triazolo [4,5-β]pyridinium 3-oxid hexafluorophosphate (HATU), N,N'-Diisopropylcarbodiimide (DIC) and 1-Hydroxybenzotriazole.

Dimethylformamide (DMF) and Dichloromethane (DCM) were purchased from Sigma-Aldrich.

Fmoc-21-amino-4,7,10,13,16,19-hexaoxaheneicosanoic acid (Fmoc-PEG12-OH) was purchased from PolyPeptide Laboratories.

Conjugates H-SEQ ID NO: 1-NH2, H-βAla-PEG12-SEQ ID NO: 1-NH2 and H-βAla-PEG12-SEQ ID NO: 13-NH2 were synthesized by solid phase peptide synthesis (SPPS) method using a Fmoc/tBu strategy and a Fmoc-Rink Amide Resin (100-200 mesh, 1% DVB, loading 0.7 mmol/g) purchased from Iris Biotech. Such a resin allows synthesis of peptides completely deprotected on their side chains and having a C-terminal amide.

Peptide synthesis was performed on a Liberty™ (CEM) microwave synthesizer for cMThzRLRGPen (SEQ ID NO: 1) and cRPLGRMC (SEQ ID NO: 13) sequences while linkers Fmoc-βAla-OH and Fmoc-PEG12-OH were coupled manually, when concerned.

For automated synthesis, amino acids were coupled via micro-wave activation of the acid function of the n+1 amino acid using aa/DIEA/HATU: 4/4/8 equivalent (with respect to the resin) in a 0.25 mmol scale synthesis. Coupling time was adjusted to 10 min. Double couplings were necessary for amino acids introduced after Thiazolidine or Proline residues. Deprotection of the Fmoc group of a new amino acid thus coupled was carried out using 20% piperidin in DMF. The last amino acid coupled during peptide elongation was deprotected to enable further coupling on the N-terminus. For the sequences with a linker introduced in between the cage and the peptide vector, Fmoc-PEG12-OH was then introduced manually using aa/DIC/HOBt: 1.5/4/2 equivalent (with respect to the resin). Reaction was performed overnight at room temperature. A TNBS test allowed to monitor the coupling efficiency. After Fmoc deprotection with a solution Piperidin/DMF (20%, 3*5 min), Fmoc-βALa-OH was finally conjugated to the free N-terminus using aa/DIEA/COMU: 3/8/3 equivalent for 3 h at room temperature. A TNBS test allowed to monitor the coupling efficiency and Fmoc was removed with a 20% piperidin solution in DMF (3*5 min).

Resin-bound peptides were cleaved using a solution comprised of TFA/TIS/H2O/EDT: 94/2/2/2 for at least 2 hours at room temperature (RT). A minimum of 15 mL of cleavage solution were used per gram of resin. Crude peptides were then precipitated using ice-cold ether, centrifuged at 3000 rpm for 8 min and lyophilized in H2O/0.1% TFA. White solids were obtained and engaged in the next step without any further purification.

Cyclization of Conjugates H— SEQ ID NO: 1-NH$_2$, H-βAla-PEG12-SEQ ID NO: 1-NH$_2$ and H-βAla-PEG12-SEQ ID NO: 13-NH$_2$:

Disulfide bridges were obtained by intramolecular cyclization from two thiol functions of two suitably protected Cys or Pen, either in configuration L or D. AcOH, K3[Fe(CN)6] and ammonium carbonate were purchased from Sigma-Aldrich. Crude H— SEQ ID NO: 1-NH$_2$, H-βAla-PEG12-SEQ ID NO: 1-NH$_2$ and H-βAla-PEG12-SEQ ID NO: 13-NH$_2$ conjugates were dissolved in AcOH 0.5% to get a 0.5 mg/mL final concentration. Ammonium carbonate (2N) was added to the peptide solutions to reach an approximate basic pH of 8-9. K3[Fe(CN)6] (0.01N) was then added to the reaction mixtures until a bright and persistent yellow color was observed. Monitoring of the reactions was performed by analytical RP-HPLC. Usually reactions were quantitative in less than 30 min. Reaction mixtures were filtered on a 0.45 µm membrane and purified by preparative RP-HPLC. Fractions with purities above 95% were collected and lyophilized to give pure white powders (final purity>95%). The homogeneity and identity of the pure synthetic peptides were assessed by analytical RP-HPLC. Peptides were satisfactorily checked for identity by ESI mass spectrometry on LCQ Fleet (ThermoFisher) used in positive mode.

NODAGA and DOTA Conjugation to H— SEQ ID NO: 1-NH$_2$, H-βAla-PEG12-SEQ ID NO: 1-NH2 and H-βAla-PEG12-SEQ ID NO: 13-NH2:

The chelators were conjugated to the peptides using the activated esters of NODAGA mono-N-hydroxysuccinimide (NODAGA-NHS) and DOTA mono-N-hydroxysuccinimide (DOTA-NHS).

NODAGA-NHS and DOTA-NHS were obtained from Chematech (Dijon, France).

To a peptide solution in DMF (1.2 mM) was added the chelating agent (4 eq) and DIEA (10 eq). The reaction mixture was allowed to stir at room temperature. Monitoring of the reaction by analytical RP-HPLC assessed that the reaction was quantitative. Reaction mixtures were filtered on a 0.45 µm membrane and purified by preparative RP-HPLC. Fractions with purities above 95% were collected and lyophilized to give pure white powders (final purity>95%). The homogeneity and identity of the pure synthetic peptides were assessed by analytical RP-HPLC. Peptides were satisfactorily checked for identity by ESI mass spectrometry on LCQ Fleet (Thermo Fisher) used in positive mode.

Example 7: Surface Plasmon Resonance (SPR) Determination of MG04/VH-DO35, CH44, FG770, CH40 and FG769 Affinity ($K_D$) for LDLR Affinity ($K_D$) of Conjugates for LDLR Recombinant human LDLR (His-tagged) was purchased from Sino Biological (Beijing, China). Interaction of conjugates with LDLR was tested at 25° C. using a Biacore T200 (GE Healthcare) and 50 mM HEPES-NaOH pH7.4, 150 mM NaCl, 0.005% Tween-20, 50 µM EDTA as running buffer. hLDLR was immobilized on a NiHC sensor chip (Xantec, Dusseldorf, Germany) at a density of 35-60 fmol/mm$^2$. Binding of conjugates to LDLR-coated flow cells was corrected for non-specific binding to uncoated flow cells. The single-cycle kinetic method was used to measure the affinity of ligands with LDLR. Ligands were diluted in running buffer and injected sequentially 2 minutes at 30 µl/min using increasing concentrations. Blank run injections of running buffer were performed in the same conditions before ligand injection. Double-subtracted sensorgrams were globally fitted with the 1:1 Langmuir binding model from Biacore T200 Evaluation version 2.0. $K_{Ds}$ are summarized in the following table II:

TABLE II

Affinity for LDLR of conjugates CH40, FG769, CH44, FG770 and MG04.

| Conjugate name/ID | kon (M$^{-1}$s$^{-1}$) | koff (s$^{-1}$) | $K_D$ (nM) |
|---|---|---|---|
| CH44 | 2.84E+06 | 6.73E−02 | 23.7 |
| CH40 | | No Binding | |
| FG770 | 3.72E+05 | 4.01E−02 | 108 |
| FG769 | | No Binding | |
| MG04 ou VH-DO35 | 3.72E+06 | 5.59E−02 | 16.6 |

Example 8: PET Imaging of $^{68}$Ga-CH44 and its Scrambled Counterpart $^{68}$Ga-CH40 in a Subcutaneous Mouse Model of Adrenal Gland Tumour The objective in this example was to use PET-Scan to assess the biodistribution of a conjugate targeting the LDLR ($^{68}$Ga-CH44) and its scrambled counterpart ($^{68}$Ga-CH40) following intravenous administration to mice implanted with adrenal cancer (xenograft model). $^{18}$F-FDG was used as control.

Materials
Radiolabelling

CH44 and CH40 were radiolabelled using $^{68}$Ga chloride. Gallium was obtained in $^{68}$Ga$^{3+}$ form using a commercial TiO$_2$-based $^{68}$Ge/$^{68}$Ga generator (Obninsk). A radiolabeling reaction was conducted by reacting 20 μg of NODAGA-CH44 and 40 μg NODAGA-CH40 with 74-148 MBq (2-4 mCi) of $^{68}$Ga in 200 μL of ammonium acetate buffer (4M, pH 6) at 25° C. for 15 minutes.

The specific activity obtained for $^{68}$Ga-CH44 and $^{68}$Ga-CH40 were 12.5 Bq/mmol and 5.5 Bq/mmol respectively.

Tumour Implantation

Animal studies were performed according to the protocols approved by the Aix-Marseille Ethic comity (Comity 14). Four weeks old BALB/c Nude Mouse male were obtained from Charles River Inc. Mice were implanted subcutaneously in the upper flanks with NCI-H295R cells (7×10$^6$) in 150 μL of complete medium containing 50% Matrigel (Corning). Mice were used for imaging experiments when the tumours reached a volume comprised between 700-1500 mm$^3$.

Administration Route, Dose and Experimental Design

Animals received the test substance by intravenous single bolus at dose of 10±4 MBq of $^{68}$Ga-CH44 or $^{68}$Ga-CH40.

Six mice were implanted with NCI-H295R adrenal cancer cells. On day 14 following implantation, the animals were administered intravenously at 24 hours interval with $^{18}$F-FDG, $^{68}$Ga-CH44 and $^{68}$Ga-CH40, respectively. On days 32 post-implantation, the animals were administered intravenously with $^{68}$Ga-CH44 followed 24 hours later with $^{68}$Ga-CH40. Following each administration, the biodistribution in the adrenal cancer xenograft and other tissues was assessed using PET-imaging.

PET-Scan

Groups (n=5-7) of nude mice were i.v. administered 10±4 MBq of $^{68}$Ga-CH44 and PET/CT scans were acquired at 1 h post injection (p.i.). PET and PET/CT studies were performed on a microPET/microCT rodent model scanner (nanoPET/CT®, Mediso). Anesthesia was induced with 5% isoflurane and maintained at 1.5%. To improve image quality, 20 million coincidence events per mouse were acquired for every static PET emission scan (energy window, 400-600 keV; time: 20 minutes for one FOV). For dual modality PET/CT, CT images (35 kVp, exposure time of 350 ns and medium zoom) were obtained, and anatomical registration, as well as attenuation of correction, was applied to the corresponding PET scans. Six hours after the first injection, the same group of nude mice was administered 10±4 MBq of $^{68}$Ga-CH40 and PET/CT scans were acquired at 1 hour post-injection (p.i.), this series of acquisition constituted our control group.

Results
PET Imaging

Figure 6A:
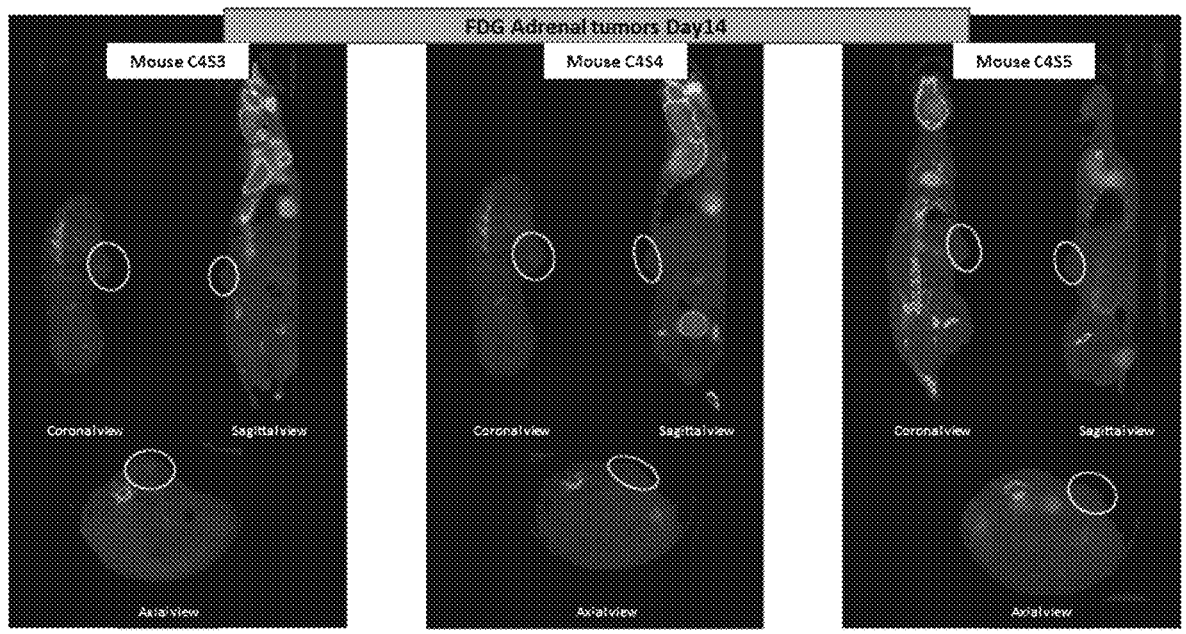
FIG. 6: PET imaging of mice administered with $^{18}$F-FDG (A), $^{68}$Ga-CH44 (B) and $^{68}$Ga-CH40 (C) at day 14 after implantation with NCI-H295R cells. The adrenal tumour is indicated by a circle.

Image acquisition was performed on day 14 for all the three compounds and on days 32 for $^{68}$Ga-CH44, $^{68}$Ga-CH40. At day 14, imaging pictures of animals injected with $^{18}$F-FDG showed no significant accumulation at the tumour site (FIG. 6A).

In contrast, on days 14 (FIGS. 6B and C) and 32 (FIGS. 7A and B), imaging pictures showed in most animals a significant accumulation of $^{68}$Ga-CH44 compared to $^{68}$Ga-CH40.

Conclusion

Experiments showed in most animals a clear and selective imaging and labelling of adrenal cancer with $^{68}$Ga-CH44 at day 14 and 32.

Example 9: PET Imaging of $^{68}$Ga-FG770 and its Scrambled Counterpart $^{68}$Ga-FG769 in a Subcutaneous Mouse Model of Adrenal Gland Tumour The objective in this example was to use PET-Scan to assess the biodistribution of a conjugate targeting the LDLR ($^{68}$Ga-FG770) and its scrambled counterpart ($^{68}$Ga-FG769) following intravenous administration to mice implanted with adrenal cancer (xenograft model). The cage used in this study was DOTA instead of NODAGA.

Materials
Radiolabelling

FG770 and FG769 were radiolabelled using $^{68}$Ga chloride. Gallium was obtained in $^{68}$Ga$^{3+}$ form using a commercial TiO$_2$-based $^{68}$Ge/$^{68}$Ga generator (Obninsk). A radiolabeling reaction was conducted by reacting 20 μg of DOTA-FG770 and 20 μg DOTA-FG769 with 74-148 MBq (2-4 mCi) of $^{68}$Ga in 100 μL of ammonium acetate buffer (2M, pH 4,5) at 95° C. for 15 minutes.

The specific activities obtained for $^{68}$Ga-FG770 and $^{68}$Ga-FG769 were 6.45 Bq/mmol and 6.16 Bq/mmol, respectively.

Tumour Implantation

Animal studies were performed according to the protocols approved by the Aix-Marseille Ethic comity (Comity 14). Four weeks old BALB/c Nude Mouse male were obtained from Charles River Inc. Mice were implanted subcutaneously in the upper flanks with NCI-H295R cells (7×10$^6$) in 150 μL of complete medium containing 50% Matrigel (Corning). Mice were used for imaging experiments when the tumours reached a volume comprised between 700-1500 mm$^3$.

Administration Route, Dose and Experimental Design

Animals received the test substance by intravenous single bolus at dose of 10±4 MBq of $^{68}$Ga-FG770 or $^{68}$Ga-FG769.

Six mice were implanted with NCI-H295R adrenal cancer cells. On day 37 following implantation, the animals were administered intravenously at 24 hours interval with $^{68}$Ga-FG770 and $^{68}$Ga-FG769, respectively. Following administration, the biodistribution in the adrenal cancer xenograft and other tissues was assessed using PET-imaging.

PET-Scan

Groups (n=3) of nude mice were administered intravenously with 10±4 MBq of $^{68}$Ga-FG770 and PET/CT scans were acquired at 1 h post injection (p.i.). PET and PET/CT studies were performed on a microPET/microCT rodent model scanner (nanoPET/CT®, Mediso). Anesthesia was induced with 5% isoflurane and maintained at 1.5%. To improve image quality, 20 million coincidence events per mouse were acquired for every static PET emission scan (energy window, 400-600 keV; time: 20 minutes for one FOV). For dual modality PET/CT, CT images (35 kVp, exposure time of 350 ns and medium zoom) were obtained, and anatomical registration, as well as attenuation correction, was applied to the correspondent PET scans.

24 hours after the first injection, the same group of nude mice was administered intravenously with 10±4 MBq of $^{68}$Ga-FG769 and PET/CT scans were acquired at 1 h and 4 h post injection (p.i.), Quantitative region-of-interest (ROI) analysis of the PET images was performed on the attenuation and decay corrected PET images using Interviewfusion.

Results

PET Imaging

Image acquisition was performed on day 37 for both compounds $^{68}$Ga-FG770 and $^{68}$Ga-FG769. Imaging pictures showed in most animals a significant accumulation of $^{68}$Ga-FG770 compared to $^{68}$Ga-FG769 (FIGS. 8A and 8B, respectively).

Conclusion

Experiments showed in most animals a clear and selective imaging and labelling of adrenal cancer with $^{68}$Ga-FG770 at day 37.

Example 10: PET Imaging of $^{68}$Ga-CH44 and its Scrambled Counterpart $^{68}$Ga-CH40 in a Subcutaneous Mouse Model of Pancreatic Cancer The objective in this example was to use PET-Scan to assess the biodistribution of a conjugate targeting the LDLR ($^{68}$Ga-CH44) and its scrambled counterpart ($^{68}$Ga-CH40) following intravenous administration to mice implanted with pancreatic cancer (xenograft model). $^{18}$F-FDG was used as control.

Materials

Radiolabelling

CH44 and CH40 were radiolabelled using $^{68}$Ga chloride. Gallium was obtained in $^{68}$Ga$^{3+}$ form using a commercial TiO$_2$-based $^{68}$Ge/$^{68}$Ga generator (Obninsk). A radiolabeling reaction was conducted by reacting 20 μg of CH44 and 40 μg CH40 with 74-148 MBq (2-4 mCi) of $^{68}$Ga in 200 μL of ammonium acetate buffer (4M, pH 6) at 25° C. for 15 minutes.

The specific activity obtained for $^{68}$Ga-CH44 and $^{68}$Ga-CH40 were 12.5 Bq/mmol and 5.5 Bq/mmol respectively.

Tumour Implantation

Animal studies were performed according to the protocols approved by the Aix-Marseille Ethic comity (Comity 14). Four week's old BALB/c Nude Mouse male were obtained from Charles River Inc. Mice were subcutaneously implanted between the shoulders with Pk4a cells (1×10$^6$) in 150 μL of complete medium. Mice were used for imaging experiments when the tumours reached a volume comprised between 700-1500 mm$^3$.

Administration Route, Dose and Experimental Design

Animals received the test substance by intravenous single bolus at dose of 10±4 MBq of $^{68}$Ga-CH44 and $^{68}$Ga-CH40.

Mice (n=5 to 6) were implanted with Pk4a pancreatic cancer cells. On day 4 following implantation, the animals were administered intravenously at 24 hours interval with $^{18}$F-FDG, $^{68}$Ga-CH44 and $^{68}$Ga-CH40, respectively. On day 12 post-implantation, the animals were administered intravenously with $^{68}$Ga-CH44 followed 24 hours later with $^{68}$Ga-CH40.

Following each administration, the biodistribution in the pancreatic cancer xenograft and other tissues was assessed using PET-imaging.

PET-Scan

Groups (n=5 to 7) of nude mice were i.v. administered 10±4 MBq of $^{68}$Ga-CH44 and PET/CT scans were acquired at 1 hour post injection (p.i.). PET and PET/CT studies were performed on a microPET/microCT rodent model scanner (nanoPET/CT®, Mediso). Anesthesia was induced with 5% isoflurane and maintained at 1.5%. To improve image quality, 20 million coincidence events per mouse were acquired for every static PET emission scan (energy window, 400-600 keV; time: 20 minutes for one FOV). For dual modality PET/CT, CT images (35 kVp, exposure time of 350 ns and medium zoom) were obtained, and anatomical registration, as well as attenuation of correction, was applied to the correspondent PET scans. Six hours after first injection, the same group of nude mice was administered 10±4 MBq of $^{68}$Ga-CH40 and PET/CT scans were acquired at 1 hour post injection (p.i.), this series of acquisition constituted the control group.

Results

PET Imaging

Figure 9A:
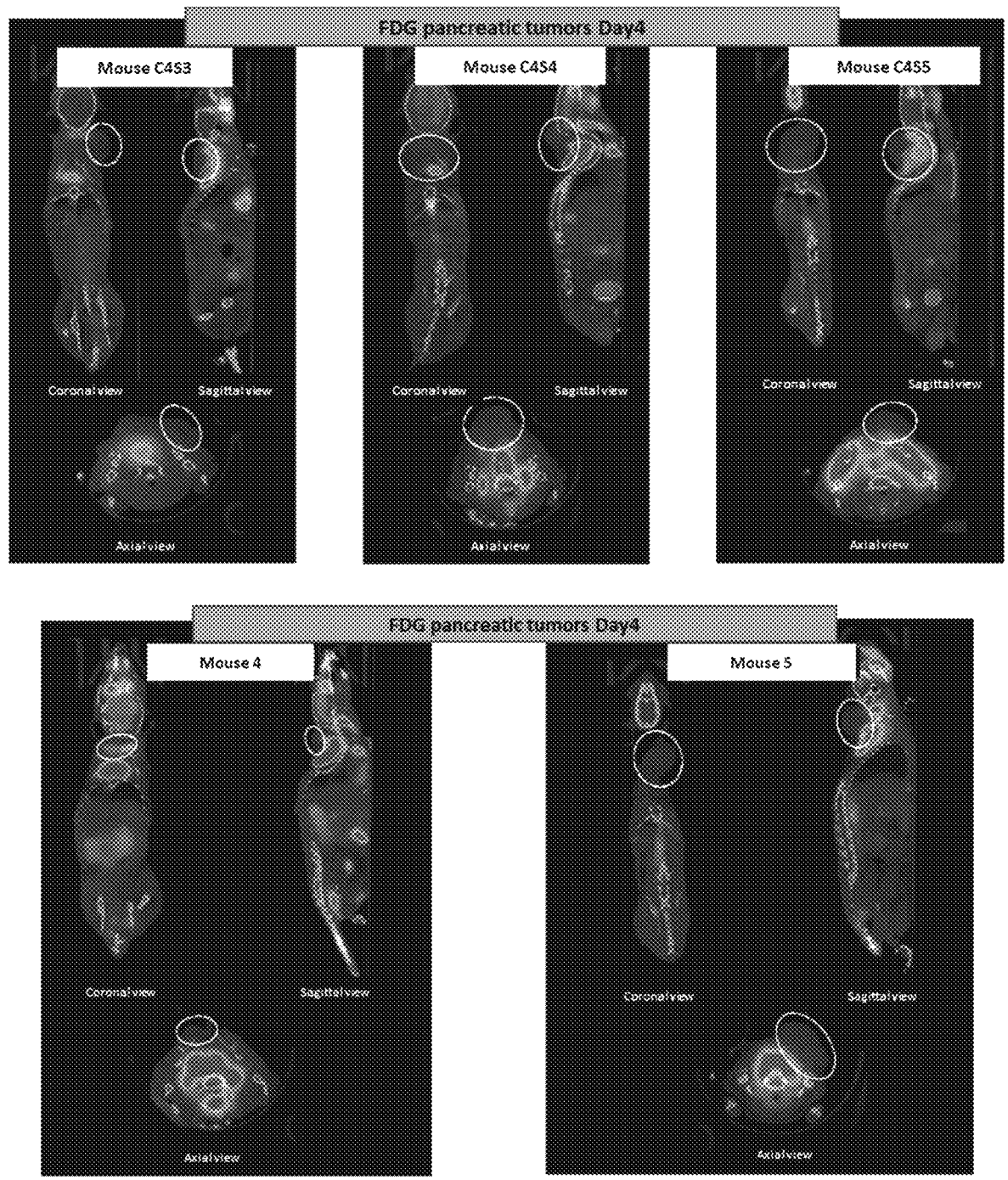
FIG. 9: PET imaging of mice administered with $^{18}$F-FDG (A), $^{68}$Ga-CH44 (B) and $^{68}$Ga-CH40 (C) at day 4 after implantation with Pk4a cells. The pancreatic tumour is indicated by a circle.
Figure 9B:
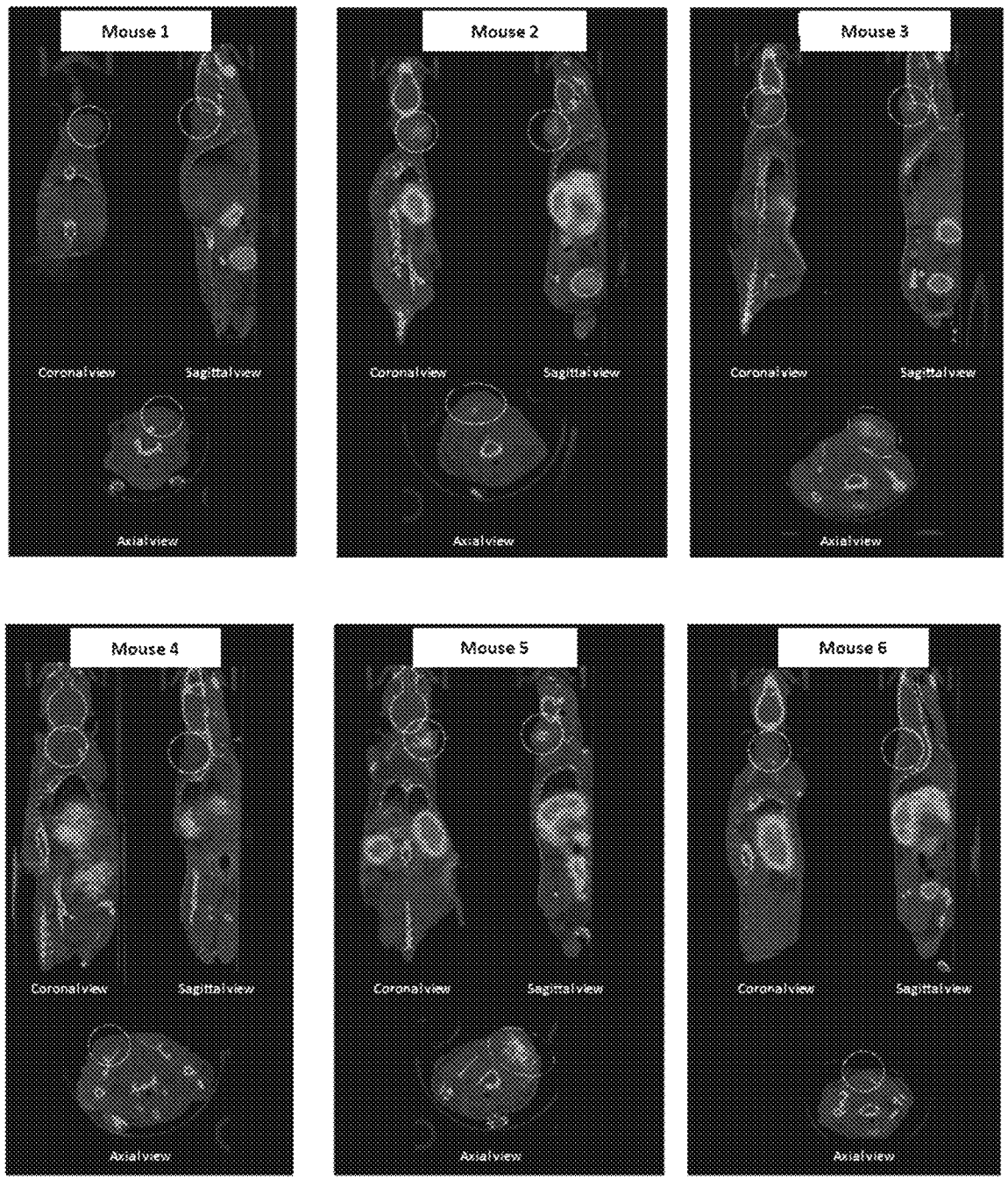
Figure 9C:
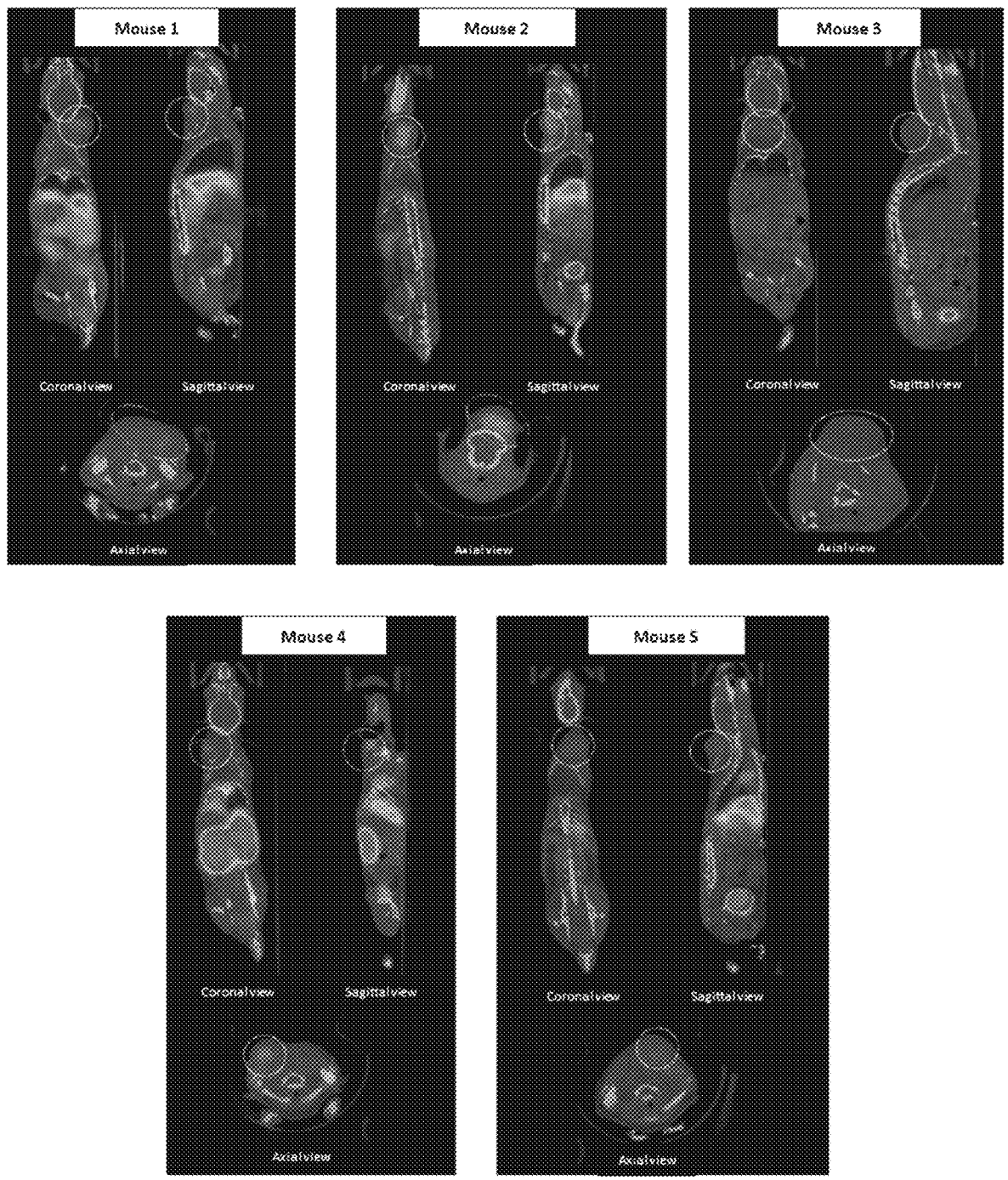
Figure 10A:
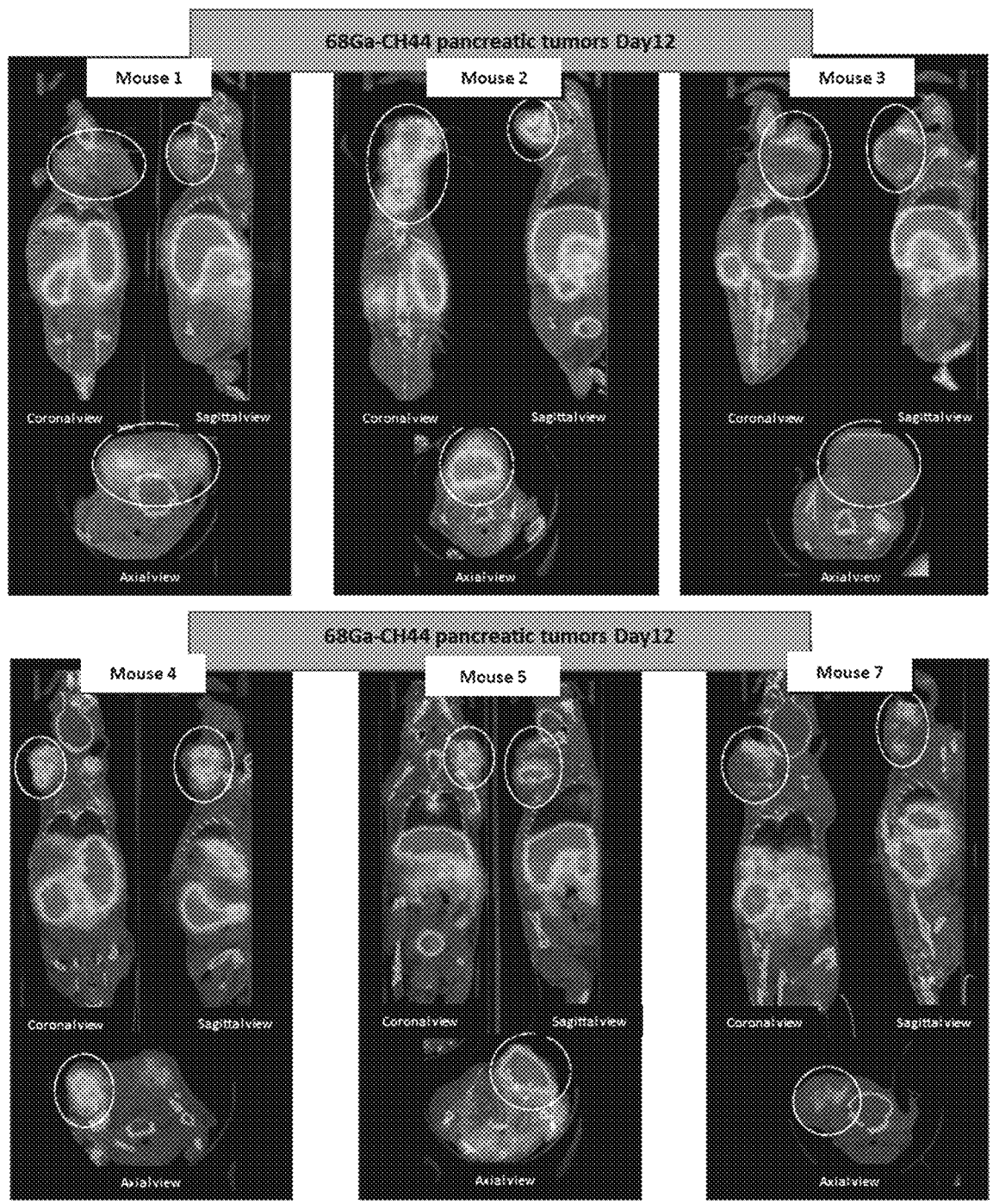
FIG. 10: PET imaging of mice administered with $^{68}$Ga-CH44 (A) and $^{68}$Ga-CH40 (B) at day 12 after implantation with Pk4a cells. The pancreatic tumour is indicated by a circle.
Figure 10B:
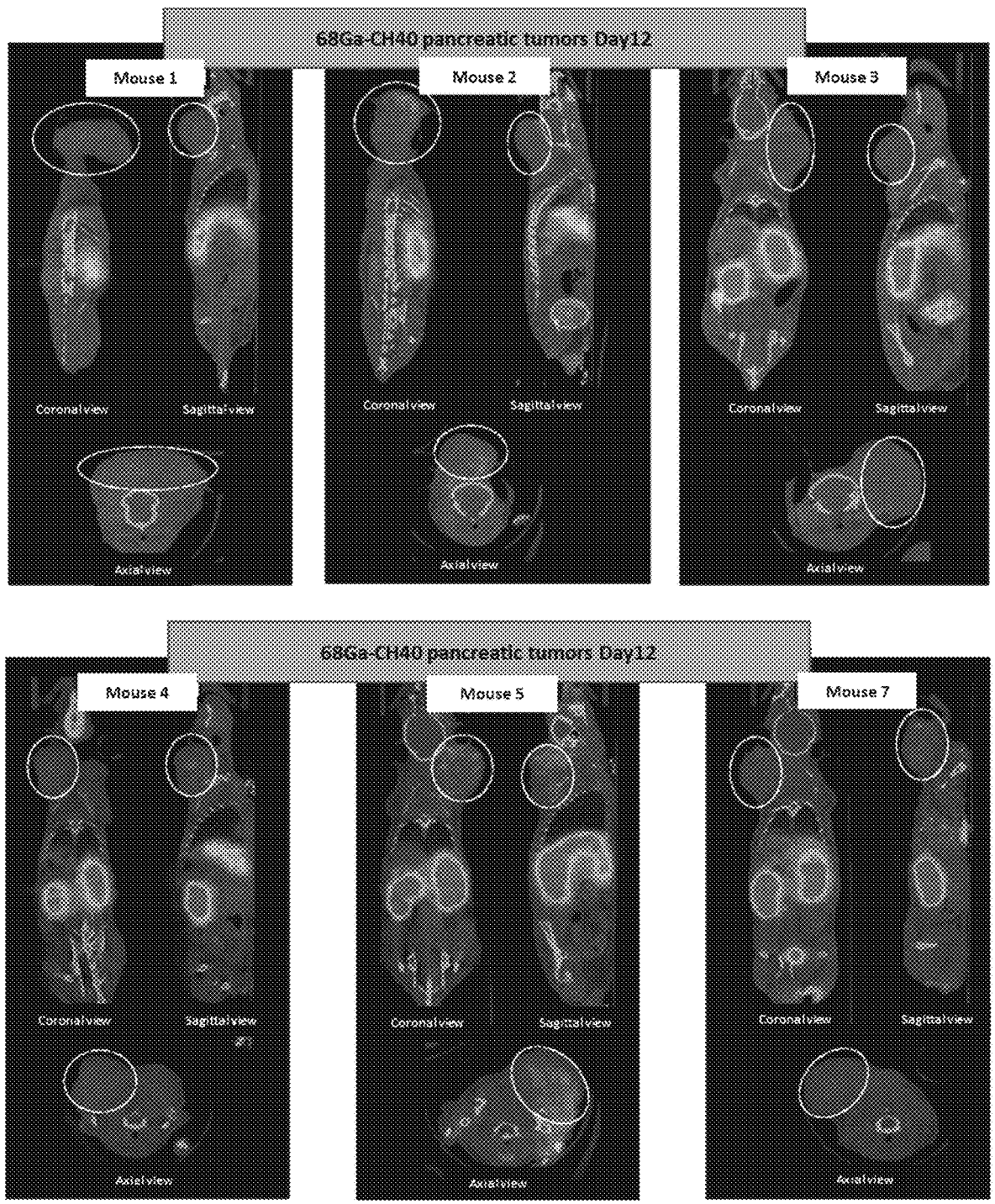

Image acquisition was performed on day 4 for $^{18}$F-FDG, $^{68}$Ga-CH44 and $^{68}$Ga-CH40 and day 12 for $^{68}$Ga-CH44 and $^{68}$Ga-CH40. There was no significant accumulation of the various compounds at day 4 due to the small size of the tumour (FIGS. 9A to 9C, respectively). However, imaging pictures showed in most animals a significant accumulation of $^{68}$Ga-CH44 in comparison of $^{68}$Ga-CH40 at days 12 (FIGS. 10A to 10B, respectively).

Conclusion

Experiments showed a clear and selective imaging and labelling of pancreatic cancer with $^{68}$Ga-CH44 at day 12.

Example 11: PET Imaging of $^{68}$Ga-CH44 and its Scrambled Counterpart $^{68}$Ga-CH40 in an Orthotopic Mouse Model of Glioblastoma The objective in this example was to assess using PET-Scan the biodistribution of a conjugate targeting LDLR ($^{68}$Ga-CH44) and its scrambled counterpart ($^{68}$Ga-CH40) following intravenous administration to mice implanted with glioblastoma (xenograft model). A comparison was also carried out at day 21 against $^{68}$Ga-RGD, an integrin specific marker used in several clinical investigations for glioblastoma.

Materials

Radiolabelling

CH44 and CH40 were radiolabelled using $^{68}$Ga chloride. Gallium was obtained in $^{68}$Ga$^{3+}$ form using a commercial TiO$_2$-based $^{68}$Ge/$^{68}$Ga generator (Obninsk). A radiolabeling reaction was conducted by reacting 20 μg of CH44 and 40 μg CH40 with 74-148 MBq (2-4 mCi) of $^{68}$Ga in 200 μL of ammonium acetate buffer (4M, pH 6) at 25° C. for 15 minutes.

The specific activity obtained for $^{68}$Ga-CH44 and $^{68}$Ga-CH40 were 12.5 Bq/mmol and 5.5 Bq/mmol respectively. The specific activity for $^{68}$Ga-RGD was 7.35 Bq/mmol.

Tumour Implantation

Animal studies were performed according to the protocols approved by the Aix-Marseille Ethic comity (Comity 14). Six week's old BALB/c Nude Mouse male were obtained from Charles River Inc. Mice were implanted in brain Striatum (1 mm anterior, 2 mm lateral to the bregma and 3 mm of depth) with U87MG cells (5×10$^5$) in 5 μL of PBS. Mice were used for imaging experiments at J14 and J21 post injection, with an expected volume of 9 and 53 mm$^3$ respectively.

Administration Route, Dose and Experimental Design

Animals received the test substance by intravenous single bolus at dose of 8±4 MBq of $^{68}$Ga-CH44 and $^{68}$Ga-CH40.

Mice (n=6) were implanted with U87MG glioblastoma cells. On day 14 following implantation, the animals were administered intravenously at 24 hours interval with $^{68}$Ga-CH44 and $^{68}$Ga-CH40, respectively. On day 21 post-implantation, the animals were administered intravenously at 24 hours and 72 hours interval with $^{168}$Ga-CH44, $^{68}$Ga-CH40 and $^{68}$Ga-RGD, respectively.

Following each administration, the biodistribution in the glioblastoma cancer and other tissues was assessed using PET-imaging.

PET-Scan

Mice (n=6) of nude mice were i.v. administered 8±4 MBq of $^{68}$Ga-CH44 and PET/CT scans were acquired at 1 hour post injection (p.i.). PET and PET/CT studies were performed on a microPET/microCT rodent model scanner (nanoPET/CT®, Mediso). Anesthesia was induced with 5% isoflurane and maintained at 1.5%. To improve image quality, 20 million coincidence events per mouse were acquired for every static PET emission scan (energy window, 400-600 keV; time: 20 minutes for one FOV). For dual modality PET/CT, CT images (35 kVp, exposure time of 350 ns and medium zoom) were obtained, and anatomical registration, as well as attenuation of correction, was applied to the correspondent PET scans. Six hours after first injection, the same group of nude mice was administered 8±4 MBq of $^{68}$Ga-CH40 and PET/CT scans were acquired at 1 hour post injection (p.i.), this series of acquisition constituted our control group.

Results

PET Imaging

Figure 11A:
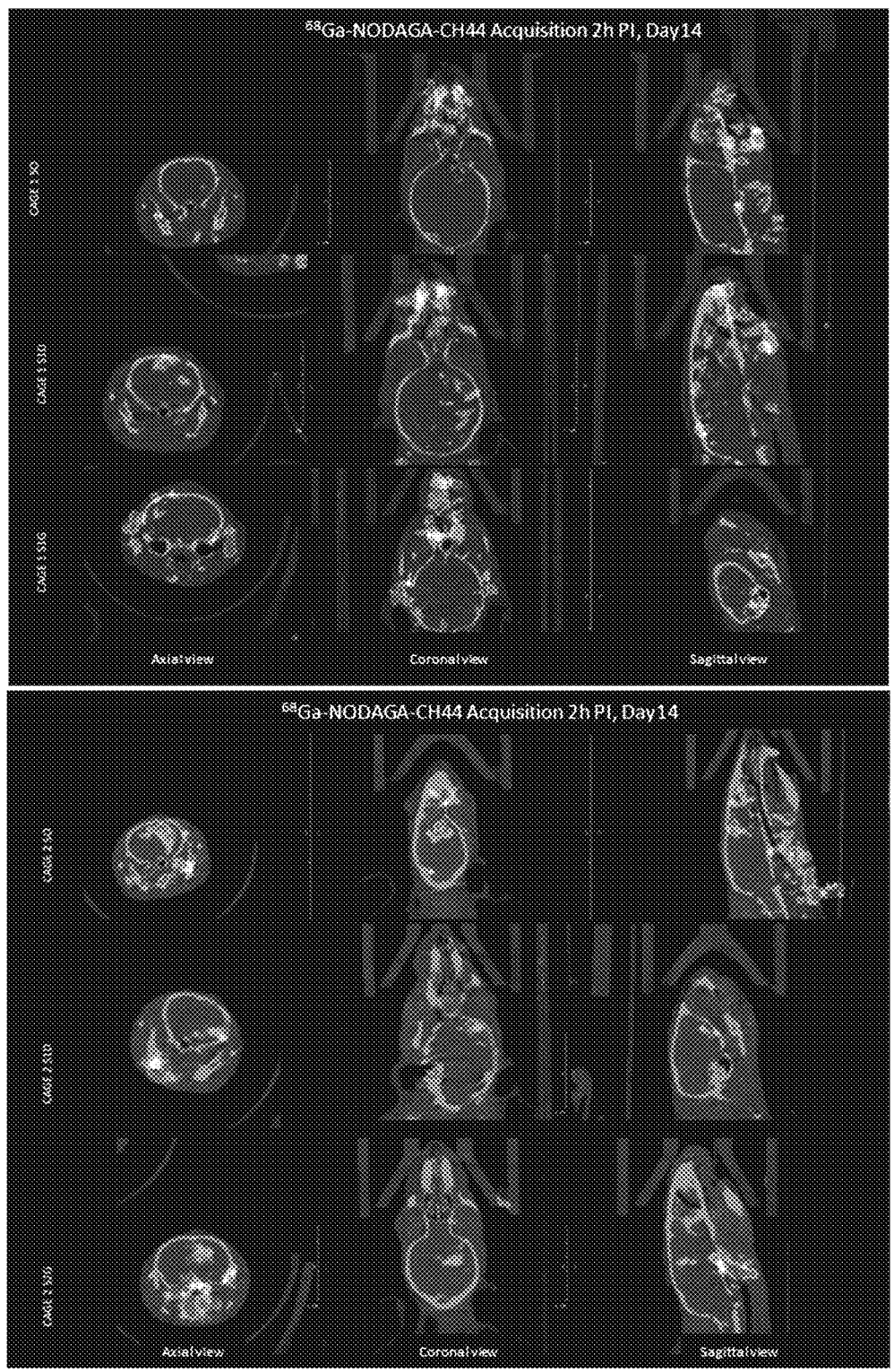
FIG. 11: PET imaging of mice administered with $^{68}$Ga-CH44 at day 14 (A), $^{68}$Ga-CH40 at day 16 (B), $^{68}$Ga-CH44 at day 21 (C), $^{68}$Ga-CH40 at day 21 (D), and $^{68}$Ga-RGD at day 21 (E) after cerebral implantation with U87MG cells.
Figure 11B:
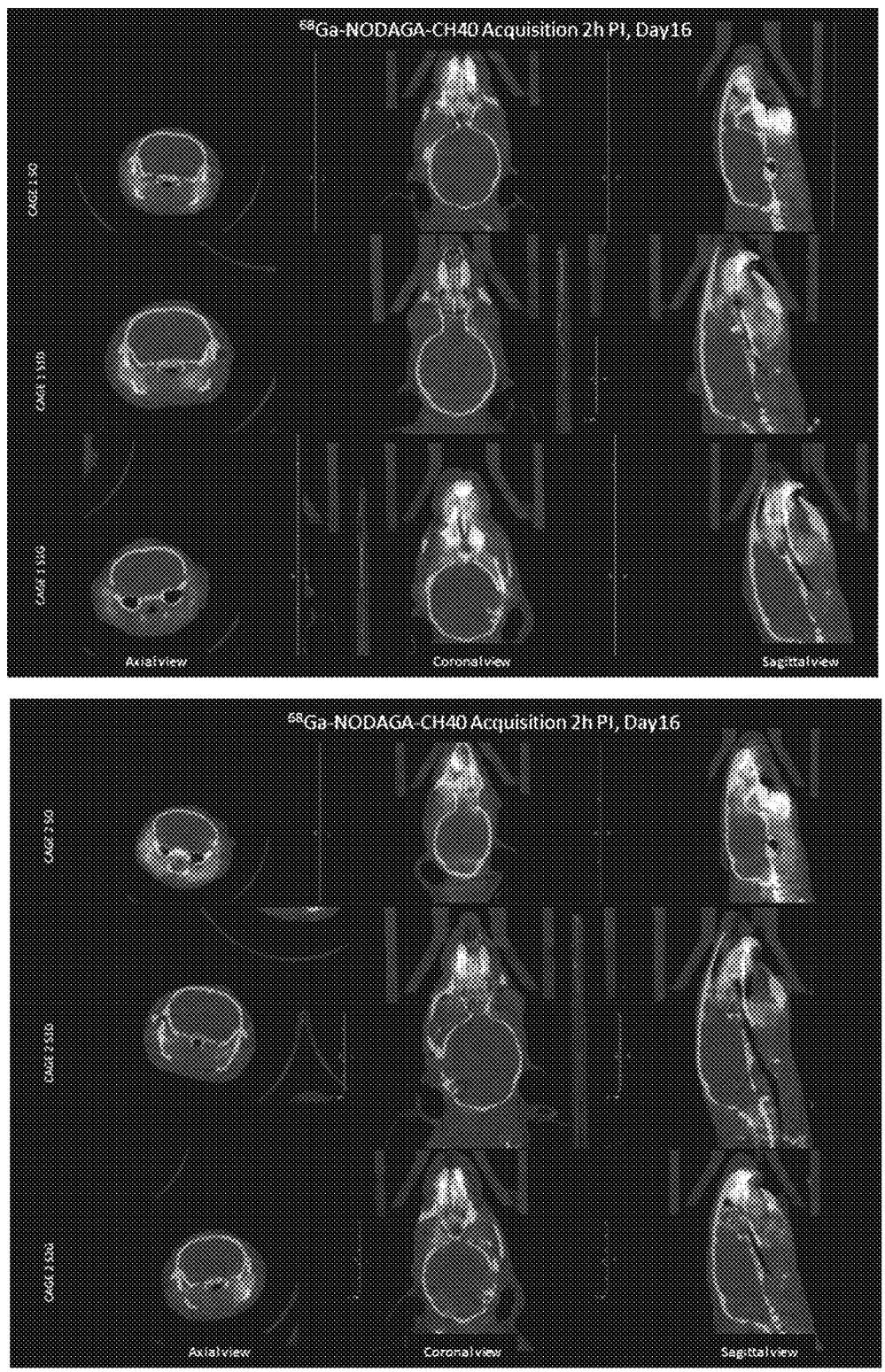
Figure 11C:
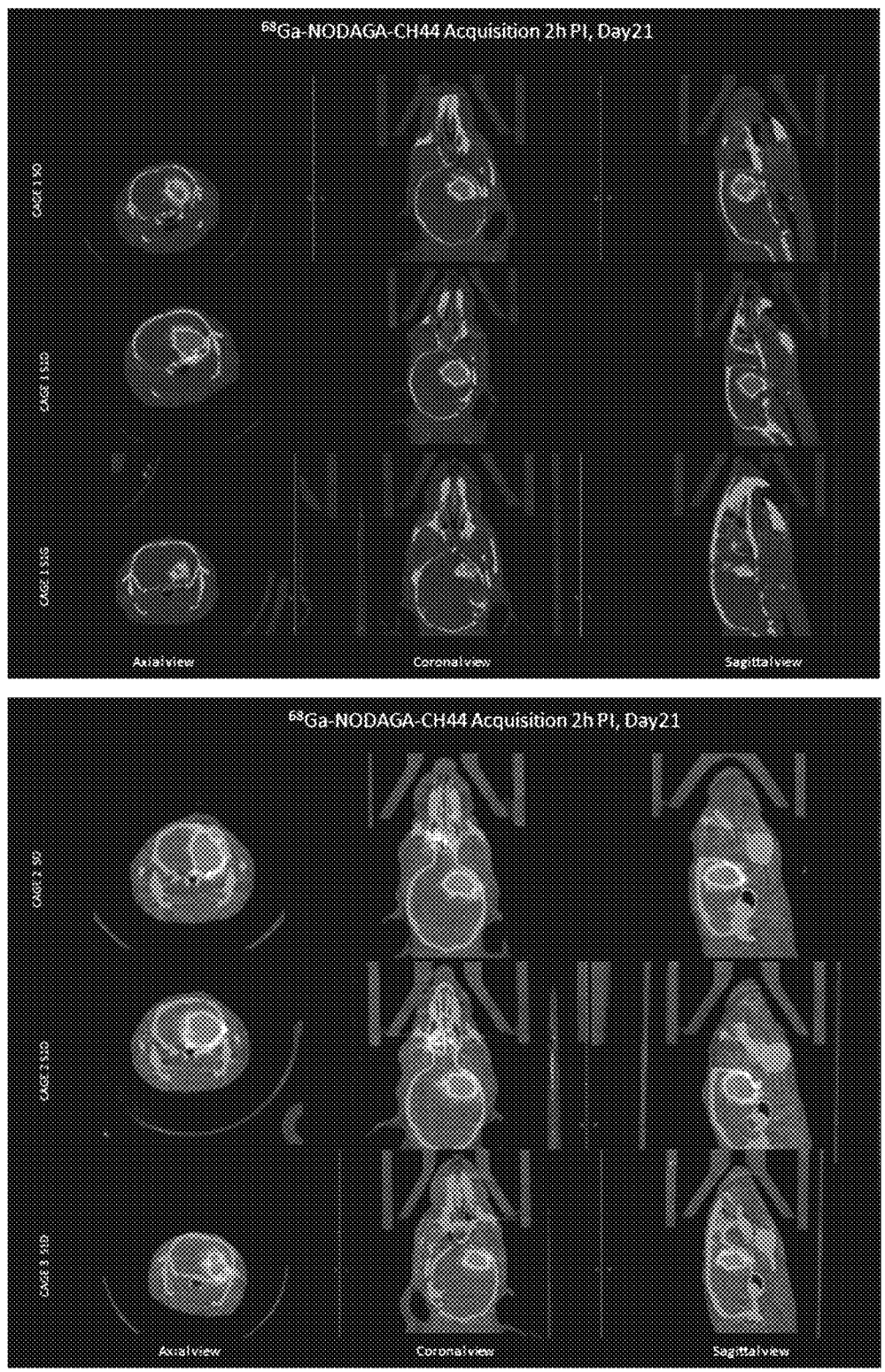
Figure 11D:
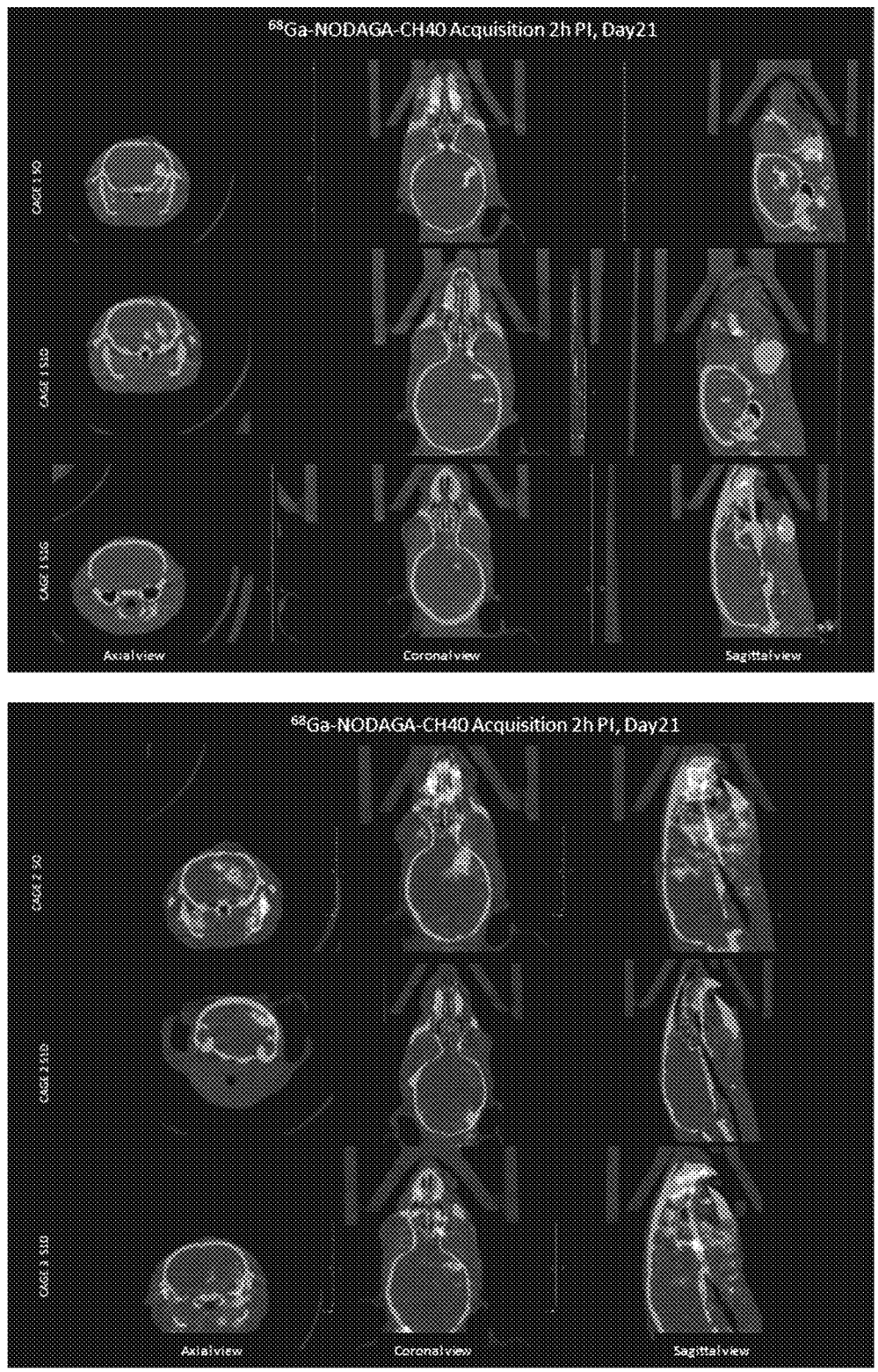
Figure 11E:
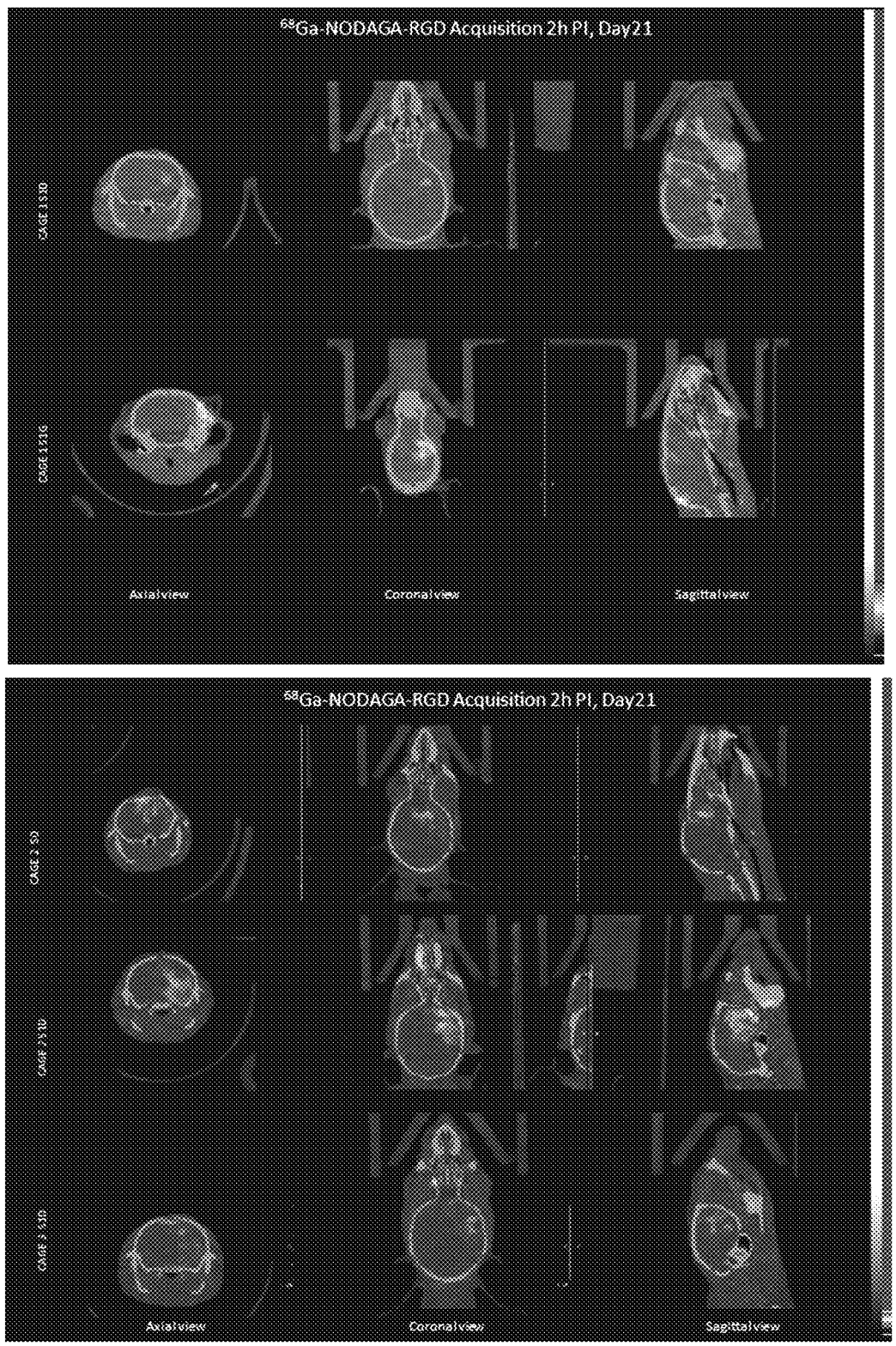
Figure 12:
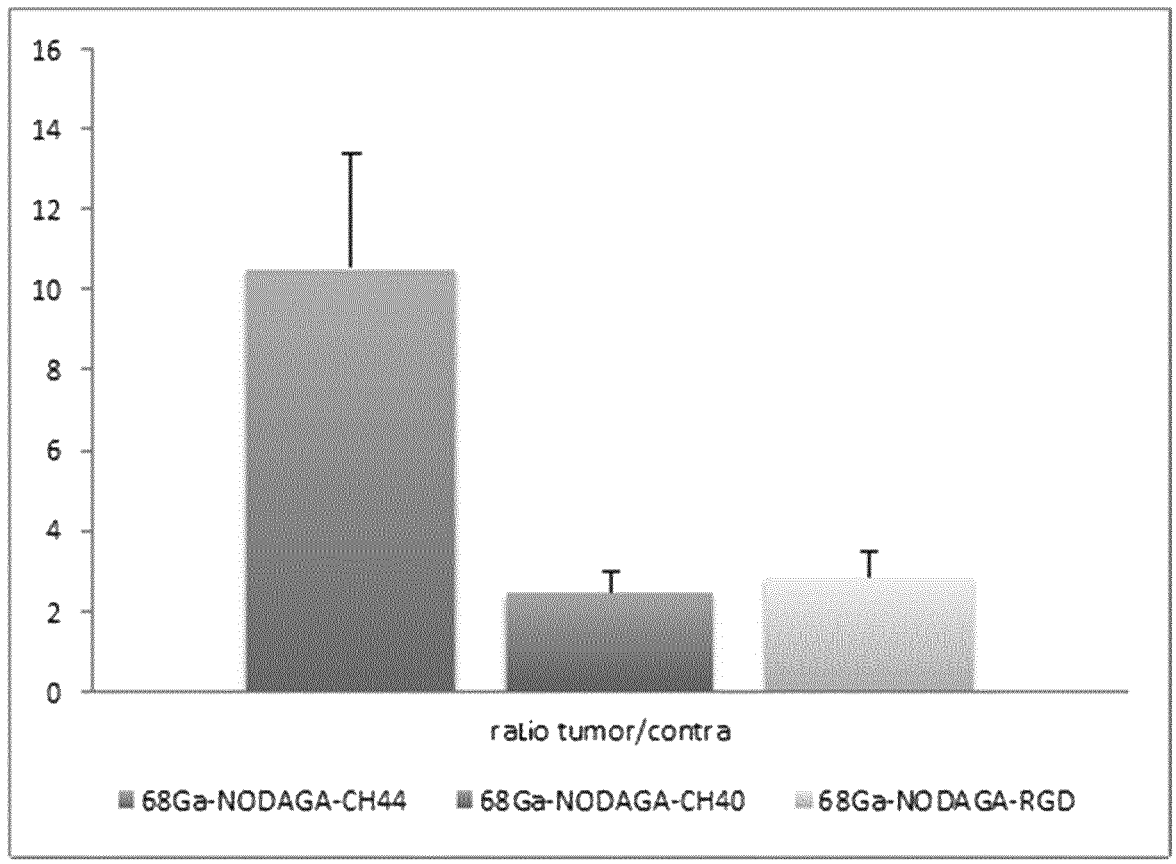
FIG. 12: Quantification of $^{68}$Ga-CH44, $^{68}$Ga-CH40 and $^{68}$Ga-RGD in animals implanted with U87MG on day 21 expressed as tumor on contra ratio.

Image acquisition was performed on day 14 for $^{68}$Ga-CH44 and $^{68}$Ga-CH40 and days 21 for $^{68}$Ga-CH44, $^{68}$Ga-CH40 and $^{68}$Ga-RGD. Imaging pictures showed for 4 of 6 mice a signal of $^{68}$Ga-CH44 on day 14, and no significant signal for $^{68}$Ga-CH40 on day 16 (FIGS. 11A and 11B, respectively). At day 21, all the 6 mice showed a high signal of $^{68}$Ga-CH44, significant stronger than the weak signal of either $^{68}$Ga-CH40 or $^{68}$Ga-RGD (FIGS. 11C, 11D, 11E, respectively). An analysis of the ratio tumour/contra was carried out in order to quantify the imaging signal. The quantification indicates that $^{68}$Ga-CH44 accumulates more significantly than $^{68}$Ga-CH40 or $^{68}$Ga-RGD (about 4-fold) (FIG. 12).

Conclusion

Experiments showed a clear and selective imaging and labelling of glioblastoma cancer with $^{68}$Ga-CH44 at day 21.

Example 12: PET Imaging of $^{68}$Ga-CH44 and $^{68}$Ga-MG04 in a Subcutaneous Mouse Model of Adrenal Cancer The objective in this example was to assess and compare using PET-Scan the biodistribution of two conjugates targeting LDLR, one with a NODAGA cage ($^{68}$Ga-CH44) and one with a DOTA cage and without a spacer (S) ($^{68}$Ga-MG04), following intravenous administration to mice implanted with subcutaneous model of adrenal cancer (xenograft model).

Materials

Radio Labelling

CH44 and MG04 were radiolabelled using $^{68}$Ga chloride. Gallium was obtained in $^{68}$Ga$^{3+}$ form using a commercial TiO$_2$-based $^{68}$Ge/$^{68}$Ga generator (Obninsk). A radiolabeling reaction was conducted by reacting 20 µg of CH44 with $^{68}$Ga in 200 µL of ammonium acetate buffer (4M, pH 6) at 25° C. for 15 minutes. A radiolabeling reaction was conducted by reacting 20 µg of MG04 with $^{68}$Ga in 200 µL of ammonium acetate buffer (pH 4) at 100° C. for 10 minutes.

The specific activity obtained for $^{68}$Ga-CH44 and $^{68}$Ga-MG04 were 331.3±10.5 MBq/g and 449.7±148.1 MBq/g respectively. The complexation performance were 91±16.9% for $^{68}$Ga-MG04 and 97±1.4% for $^{68}$Ga-CH44.

Tumour Implantation

Animal studies were performed according to the protocols approved by the University of Clermont-Auvergne. Four weeks old BALB/c Nude Mouse male were obtained from Charles River Inc. Mice were implanted subcutaneously at the bottom of the neck with NCI-H295R cells (7×10$^6$) in 150 µL of complete medium containing 50% Matrigel (Corning). Mice were used for imaging experiments when the tumours reached a volume comprised between 200-400 mm$^3$.

Administration Route, Dose and Experimental Design

Animals received the test substance by intravenous single bolus at dose of 21.6±3.6 MBq of $^{68}$Ga-CH44 or $^{68}$Ga-MG04 in a volume of 150.8±40.3 µL.

Six mice were implanted with NCI-H295R adrenal cancer cells. On day 48 following implantation, the animals were administered intravenously at 48 hours interval with $^{68}$Ga-CH44 and $^{68}$Ga-MG04, respectively. Following each administration, the biodistribution in the adrenal cancer xenograft and other tissues was assessed using PET-imaging.

PET-Scan

Groups (n=2) of nude mice were i.v. administered 21.6±3.6 MBq of $^{68}$Ga-CH44 and PET/CT scans were acquired at 1 h post injection (p.i.). PET and CT studies were performed on a microPET rodent model (eXplore Vista, GE Healthcare) and on a microCT rodent model (eXplore CT120, GE Healthcare). Anesthesia was induced with 5% isoflurane and maintained at 1.5%. To improve image quality, 20 million coincidence events per mouse were acquired for every static PET emission scan (energy window, 250-700 keV; time: 5 minutes for one FOV). For dual modality PET/CT, CT images (70 kVp, exposure time of 32 ms and medium zoom) were obtained, and anatomical registration, as well as attenuation of correction, was applied to the corresponding PET scans. Forty-eight hours after the $^{68}$Ga-CH44 injection, the same group of nude mice was administered 21.6±3.6 MBq of $^{68}$Ga-MG04 and PET/CT scans were acquired at 1 hour post-injection (p.i.), this series of acquisition constituted second group.

Results

PET Imaging

Image acquisition was performed on day 48 for $^{68}$Ga-CH44. 48 h hours later image acquisition was performed for $^{68}$Ga-MG04. On days 48 (FIG. 13A) and 50 (FIG. 13B), imaging pictures showed a significant accumulation of $^{68}$Ga-CH44 and $^{68}$Ga-MG04 (yellow arrow=tumor, blue arrow=kidney). Moreover the tumoral uptake for $^{68}$Ga-MG04 is 73% higher compare to $^{68}$Ga-CH44. Images are shown with the same threshold (SUVmin=0; SUVmax=1). SUV (Standardized Uptake Value):

$$SUV = \frac{\text{Mean } ROI \text{ activity } (MBq/\text{g})}{\text{Injected dose } (MBq)/\text{Body weight in gram}}$$

Where, $MBq$ = Mega Becquerel and g = gram.

Conclusion

Experiments showed a clear and selective imaging and labelling of adrenal cancer with the two molecules, $^{68}$Ga-MG04 and $^{68}$Ga-CH44, with an advantage on tumoral uptake for $^{68}$Ga-MG04 (73%).

The invention claimed is:

1. A conjugated compound of formula M—C—S—P, wherein:
M is $^{68}$Ga;
C is a DOTA chelator;
S is PEG$_{12}$ with or without a beta-alanine at one end; and
P is SEQ ID NO:1.

2. The conjugated compound of claim 1, wherein the compound further comprises a group T, wherein said group T is selected from prostate specific membrane antigen (PSMA), neurotensin, and analogues of somatostatin.

3. The conjugated compound of claim 1, wherein said compound is a multimer comprising two or more copies of a P or M group, or of both.

4. A composition comprising a conjugated compound according to claim 1 and a pharmaceutically acceptable diluent or excipient.

5. A method of labelling and/or detecting cancerous cells in a subject comprising administering the conjugated compound according to claim 1 to the subject, imaging the subject to detect a signal, and determining the presence and/or amount of signal present within the subject.

6. The method of claim 5, wherein the cancerous cells overexpress Low Density Lipoprotein Receptor (LDLR).

7. The method of claim 6, wherein the cancer is selected from a pancreatic cancer, an adrenal cancer or a glioblastoma.

8. The conjugated compound of claim 1, wherein S represents a PEG$_{12}$ spacer.

9. The conjugated compound of claim 1, wherein S represents PEG$_{12}$ with beta-alanine at one end.

* * * * *